United States Patent
Agrawal et al.

(10) Patent No.: US 12,417,007 B2
(45) Date of Patent: Sep. 16, 2025

(54) ELECTRONIC DEVICE DISPLAY SCREEN CUSTOMIZATION BASED ON IMAGE INFORMATION

(71) Applicant: MOTOROLA MOBILITY LLC, Wilmington, DE (US)

(72) Inventors: Amit Kumar Agrawal, Bangalore (IN); Himanshu Chug, Bangalore (IN); Aman Jain, Haryana (IN)

(73) Assignee: Motorola Mobility LLC, Chicago, IL (US)

(*) Notice: Subject to any disclaimer, the term of this patent is extended or adjusted under 35 U.S.C. 154(b) by 70 days.

(21) Appl. No.: 18/343,263

(22) Filed: Jun. 28, 2023

(65) Prior Publication Data

US 2025/0004605 A1  Jan. 2, 2025

(51) Int. Cl.
*G06F 3/0481* (2022.01)
*A61B 5/024* (2006.01)
*G06T 7/90* (2017.01)
*G06V 10/74* (2022.01)

(52) U.S. Cl.
CPC ............ *G06F 3/0481* (2013.01); *A61B 5/024* (2013.01); *G06T 7/90* (2017.01); *G06V 10/761* (2022.01); *G06T 2207/10024* (2013.01)

(58) Field of Classification Search
CPC ......... G06F 3/0481; A61B 5/024; G06T 7/90; G06T 2207/10024; G06V 10/761
See application file for complete search history.

(56) References Cited

U.S. PATENT DOCUMENTS

| | | | |
|---|---|---|---|
| 11,069,103 B1* | 7/2021 | Blackstock | G06F 16/436 |
| 2010/0330972 A1 | 12/2010 | Angiolillo | |
| 2016/0011758 A1* | 1/2016 | Dornbush | H04L 51/10 |
| | | | 715/764 |
| 2016/0048296 A1 | 2/2016 | Gan et al. | |
| 2019/0391729 A1* | 12/2019 | Josephson | G06T 11/60 |
| 2023/0129243 A1* | 4/2023 | Hunsmann | G06Q 30/0623 |
| | | | 382/100 |
| 2023/0308873 A1 | 9/2023 | Oudenhoven et al. | |
| 2024/0312103 A1 | 9/2024 | Zhang et al. | |

\* cited by examiner

*Primary Examiner* — Cao H Nguyen
(74) *Attorney, Agent, or Firm* — Isidore PLLC

(57) ABSTRACT

A method provides techniques for electronic device display screen customization based on image information. The method includes detecting, by at least one processor of an electronic device that comprises an electronic display and an image capturing device, a self-photo within received image content from the image capturing device. The method includes determining a user context from information within the received image content, and loading a customization display theme for the electronic device, based on the user context, wherein the customization display theme includes one or more theme elements.

20 Claims, 17 Drawing Sheets

ELECTRONIC DEVICE DISPLAY SCREEN CUSTOMIZATION BASED ON IMAGE INFORMATION

BACKGROUND

1. Technical Field

The present disclosure generally relates to portable electronic devices, and more specifically to portable electronic devices that support customization.

2. Description of the Related Art

Modern smartphones and tablet computers are equipped with high-resolution displays, as well as integrated digital cameras that capture high quality still pictures and videos. In addition to the camera and video features, smartphones can provide myriad other features. The features can include communication features, such as sending text messages and making voice calls. Additionally, the features can include engaging in social networking activities, internet browsing, navigation and mapping, online shopping, health and fitness, gaming, and more. As modern smartphones are useful for much more than voice calls, people often take their smartphones with them everywhere they go. Accordingly, a smartphone can also serve as an accessory for users in a wide variety of settings and activities.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
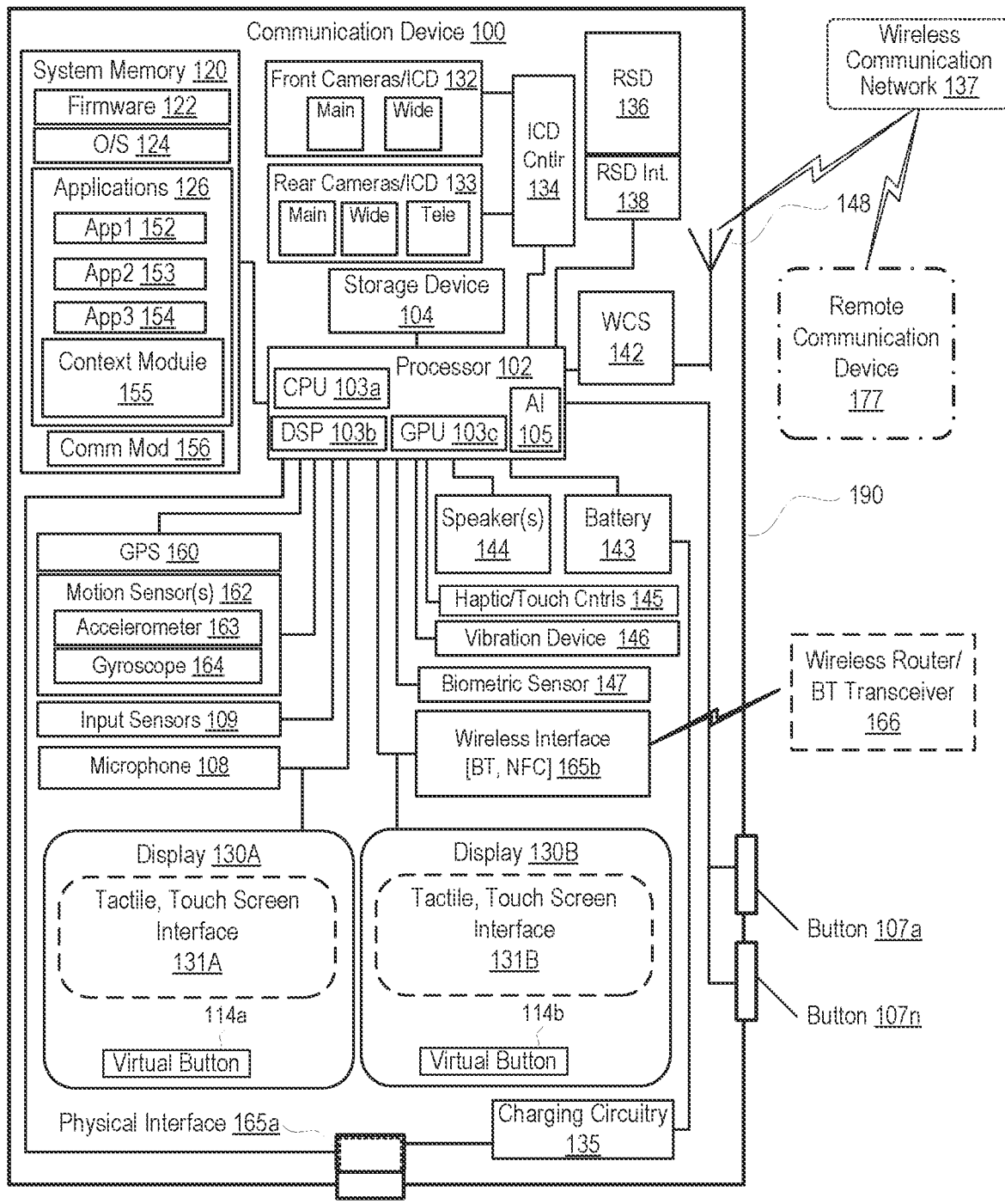
FIG. 1 depicts an example component makeup of an electronic device with a controller that can configure the device to perform customizations, according to one or more embodiments.

According to different aspects of the disclosure, an electronic device, various methods, and computer program products enable electronic device customization based on image information. Specifically, the disclosure enables an electronic device such as a smartphone, tablet computer, or the like, to provide electronic device customization based on a user context, and/or a device context. In one or more embodiments, a user context is determined from image content obtained from one or more image capturing devices (cameras) on the electronic device. The image content can contain a self-photo ('selfie'). Embodiments determine a user context based on image information in the image content. A customization display theme for the electronic device is loaded on the electronic device, based on the user context, where the customization display theme includes one or more theme elements.

According to different aspects of the disclosure, an electronic device, various methods, and computer program products enable electronic device customization based on environmental and location data. Specifically, the disclosure enables an electronic device such as a smartphone, tablet computer, or the like, to provide electronic device customization based on a user context, and/or a device context. In one or more embodiments, a device context is determined from environmental data pertaining to, or in an area of, the electronic device. The device context can include a current geographical location of the electronic device, a current meteorological condition for a current location of the electronic device, and so on. The current meteorological condition includes one or more of an outdoor temperature, precipitation, cloud conditions, and a wind speed. The device context can be based on a distance between the electronic device and another electronic device or a distance between the electronic device and a known address or location. A customization display theme for the electronic device is loaded on the electronic device, based on the device context, where the customization display theme includes one or more theme elements.

For many people, their phone is more than a communication device. It is also a form of personal expression. Since many phones these days have a similar shape, the customization of the electronic device can come from background images, such as wallpapers and lock screen images, fonts, and/or color schemes. The collection of background images, fonts, and/or color schemes that are combined for display on an electronic device are referred to as a customization display theme. Thus, a customization display theme includes one or more theme elements that correspond to the customization display theme of the electronic device. In one or more embodiments, a controller (processor) within an electronic device automatically loads (presents) a customization display theme on the display of the electronic device.

There are a wide variety of possible use cases for disclosed embodiments. One use case includes determining a user context based on detecting attire of a user taking a photo of themselves, referred to as a self-photo ('selfie'). In one or more embodiments, a controller may perform image processing techniques to analyze the attire of the user. The analysis can include determining a major color for the attire. The major color is the main, or predominant color for the attire. The analysis can include determining a formality level for the attire. The customization display theme can be created and/or selected based on the analysis of the attire. As an example, if the attire appears formal, then a conservative background and font style can be used for the electronic device. Conversely, if the attire appears casual, then a more casual, festive appearance can be selected for the customization display theme. In another example, if the attire is predominantly a particular color, e.g., green, then the customization display theme can include a similar green color for menus, borders, and/or other graphical elements.

Another use case can include determining a device context based on detecting the distance between the electronic device and a second electronic device. In one or more embodiments, this is accomplished via near-field communication radios such as Bluetooth® or the like. In response to the controller determining a second electronic device in proximity to the electronic device, a user identifier corresponding to the second electronic device is obtained. In one or more embodiments, the customization display theme can include an image, such as a photograph of the user associated with the user identifier of the second electronic device.

Another related use case can include determining a device context based on detecting the distance between the electronic device and a known address or location for a second person. In response to the controller determining the electronic device is in proximity to or approaching the known address or location, a person identifier associated with the address/location is obtained. The customization display theme can then include an image, such as a photograph of the user associated with the known address or location.

Another use case can include determining a device context based on an environmental condition, such as a meteorological condition. As an example, when the outdoor temperature is below a predetermined threshold (e.g., 5 degrees Celsius), a winter-themed customization display theme can be automatically rendered. The winter-themed customization display theme can include snowflakes, and/or other wintery elements, for example. A similar approach can be used for other meteorological conditions such as wind, precipitation, cloud cover, and so on.

Another use case can include determining a user context based on biometric information of the user. The biometric information can be obtained from the electronic device. The biometric information can include, but is not limited to, heart rate, step rate (number of steps taken per minute), breathing rate, body temperature, and/or other biometric information. A customization display theme can be loaded based on the biometric information. As an example, when a user has an elevated heart rate, a background image associated with exercise and/or fitness can be displayed on the display of the electronic device. Similarly, when the user has a resting heart rate, a different background image associated with calmness and serenity can be displayed on the display of the electronic device.

Another use case can include determining a user context based on audio information. As an example, when a user is in a noisy environment such as a nightclub where loud music is playing, disclosed embodiments may identify one or more parameters pertaining to the music, including, but not limited to, artist, title, tempo, genre, and so on. Based on the parameters, a particular customization display theme may be loaded/rendered on an electronic device. A background image can include an image of an artist that created the song, and/or other images associated with the tempo, genre, and/or other musical parameters that are detected.

In one or more embodiments, once a customization display theme is identified using one or more of the aforementioned criteria, a controller (processor) within the electronic device may transmit the customization display theme to a second electronic device, which can include a wearable computer, such as a smartwatch. In one or more embodiments, a smartwatch being worn by a user may also be loaded with a similar customization display theme. Accordingly, disclosed embodiments enable an automatically changing coordinated customization display theme that changes on both an electronic device such as a smartphone, along with an associated wearable device such as a smartwatch.

According to a first described aspect of the disclosure, there is provided an electronic device comprising: an electronic display; at least one image capturing device that captures and produces image content; a controller communicatively coupled to the at least one image capturing device and the electronic display, and which: in response to detecting a self-photo of a user in received image content from the at least one image capturing device: determines a user context from information within the received image content; and loads a customization display theme for the electronic device, based on the user context, wherein the customization display theme includes one or more theme elements.

According to another described aspect of the disclosure, there is provided an electronic device that comprises a display; a communication interface that enables the electronic device to connect to, and receive instructions from a second electronic device; a controller communicatively coupled to the display, and the communication interface, and wherein the controller: obtains, from one or more data sources, context data associated with one or more of a user and the electronic device; determines a device context based on the context data; loads a customization display theme for the electronic device, based on the device context; and presents the customization display theme within a user interface displayed on the display of the electronic device.

According to another described aspect of the disclosure, there is provided a method that enables electronic device customization based on image information. The method includes detecting, by at least one processor of an electronic device that comprises an electronic display and an image capturing device, a self-photo within received image content from the image capturing device; determining a user context from information within the received image content; and loading a customization display theme for the electronic device, based on the user context, wherein the customization display theme includes one or more theme elements. According to another described aspect of the disclosure, there is provided a method that enables electronic device customization based on environmental data. The method includes obtaining, on an electronic device, from one or more data sources, context data associated with one or more of a user and the electronic device; determining a device context based on the context data; loading a customization display theme for the electronic device, based on the device context; and presenting the customization display theme within a user interface displayed on a display of the electronic device.

According to another described aspect of the disclosure, there is provided a computer program product comprising a non-transitory computer readable medium having program instructions, that when executed by a processor of an electronic device, configures the electronic device to perform the functions of the above method processes.

The above descriptions contain simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the figures and the remaining detailed written description. The above as well as additional objectives, features, and advantages of the present disclosure will become apparent in the following detailed description.

Each of the above and below described features and functions of the various different aspects, which are presented as operations performed by the processor(s) of the electronic/communication/computing devices and/or performed by the electronic/communication/computing device are also described as features and functions provided by a plurality of corresponding methods and computer program products, within the various different embodiments presented herein. In the embodiments presented as computer program products, the computer program product includes a non-transitory computer readable storage device having program instructions or code stored thereon, which enables the communication device and/or electronic device to complete the functionality of a respective one of the above-described processes when the program instructions or code are processed by at least one processor of the corresponding electronic/communication device, such as is described above.

In the following description, specific example embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one implementation (embodiment) of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various aspects are described which may be aspects for some embodiments but not for other embodiments.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the numbered terms first, second, etc. do not denote any order or importance, but rather the terms first, second, etc. are used to distinguish one element (e.g., a person or a device) from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be provided its broadest interpretation given the context in which that term is utilized.

Those of ordinary skill in the art will appreciate that the hardware components and basic configuration depicted in the following figures may vary. For example, the illustrative components within communication device 100 (FIG. 1) are not intended to be exhaustive, but rather are representative to highlight components that can be utilized to implement the present disclosure. For example, other devices/components may be used in addition to, or in place of, the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

Referring now to the figures and beginning with FIG. 1, there is illustrated an example component makeup of communication (electronic) device 100, with specific components used to enable the device to operate in a mode to provide electronic device customization based on image data and/or environmental data, and within which various aspects of the disclosure can be implemented, according to one or more embodiments. Examples of communication device 100 include, but are not limited to, mobile devices, a notebook computer, a mobile phone, a smart phone, a digital camera with enhanced processing capabilities, a smart watch, a tablet computer, and other types of electronic devices.

Communication device 100 includes processor 102 (typically as a part of a processor integrated circuit (IC) chip), which includes processor resources such as central processing unit (CPU) 103a, communication signal processing resources such as digital signal processor (DSP) 103b, and graphics processing unit (GPU) 103c. Processor 102 can, in some embodiments, include high quality camera image signal processors (ISPs) (not shown) and dedicated artificial intelligence (AI) engines 105. Collectively, processor 102 supports computing, classifying, processing, transmitting and receiving of data and information, and presenting of graphical images within a display. Processor 102 is communicatively coupled to storage device 104, system memory 120, input devices (introduced below), output devices, including integrated displays 130A and 130B, and image capture device (ICD) controller 134. According to one or more embodiments, ICD controller 134 performs or supports functions such as, but not limited to, selecting and activating an active camera from among multiple cameras and adjusting the camera settings and characteristics (e.g., shutter speed, f/stop, ISO exposure, zoom control, field of view (FOV) angle, etc.) of the active camera.

In one or more embodiments, the functionality of ICD controller 134 is incorporated within processor 102, eliminating the need for a separate ICD controller. Thus, for simplicity in describing the features presented herein, the various camera selection, activation, and configuration functions performed by the ICD controller 134 are described as being provided generally by processor 102. Similarly, manipulation of captured images and videos are typically performed by GPU 103c and certain aspects of device communication via wireless networks are performed by DSP 103b, with support from CPU 103a. However, for simplicity in describing the features of the disclosure, the functionality provided by one or more of CPU 103a, DSP 103b, GPU 103c, and ICD controller 134 are collectively described as being performed by processor 102.

Throughout the disclosure, the term image capturing device (ICD) is utilized interchangeably to be synonymous with and/or refer to any one of front or rear facing cameras 132, 133. Front facing cameras 132 and rear facing cameras 133 are communicatively coupled to ICD controller 134, which is communicatively coupled to processor 102. Both sets of cameras 132, 133 include image sensors that can capture images that are within the field of view (FOV) of the respective ICD 132, 133. Communication device 100 can include multiple cameras having different functionality, such as a main camera capturing standard view, wide angle camera that captures a wide angle FOV, and telephoto ICD, which captures a telephoto FOV (zoom or magnified). In one or more embodiments, a single camera can be provided with camera control options to change the single camera lens to allow for wide angle and telephoto image capture. In one or more embodiments, one or more of the ICDs may be used for performing user identification via facial recognition.

System memory 120 may be a combination of volatile and non-volatile memory, such as random-access memory (RAM) and read-only memory (ROM). System memory 120 can store program code or similar data associated with firmware 122, an operating system 124, and/or applications 126. During device operation, processor 102 processes program code of the various applications, modules, OS, and firmware, that are stored in system memory 120.

In accordance with one or more embodiments, applications 126 include, without limitation, general purpose applications 152, 153, and 154, context module 155, and communication module 156. Each module and/or application provides program instructions/code that are processed by processor 102 to cause processor 102 and/or other components of communication device 100 to perform specific operations, as described herein. Descriptive names assigned to these modules add no functionality and are provided solely to identify the underlying features performed by processing of the different modules. For example, context module 155 can include program code to cause processor 102 to identify a user context and/or a device context, and load (render) a corresponding customization display theme based on the user context and/or display context.

Communication module 156 within system memory 120 enables communication device 100 to communicate with wireless communication network 137 and with other devices, such as remote communication device 177 and/or other Internet-connected devices, via one or more of audio, text, and video communications. Communication module 156 can support various communication sessions by communication device 100, such as audio communication sessions, video communication sessions, text communication sessions, receiving notifications, exchange of data, and/or a combined audio/text/video/data communication session.

In one or more embodiments, communication device 100 includes removable storage device (RSD) 136, which is inserted into RSD interface 138 that is communicatively coupled via system interlink to processor 102. In one or more embodiments, RSD 136 is a non-transitory computer program product or computer readable storage device. RSD 136 may have a version of one or more of the applications (e.g., 152, 153, 154, 156) stored thereon. Processor 102 can access RSD 136 to provision communication device 100 with program code that, when executed/processed by processor 102, the program code causes or configures processor 102 and/or generally communication device 100, to provide the various functions of detecting and removing a partial occlusion as described herein. The RSD 136 can be an example of a non-transitory or tangible computer readable storage device.

Communication device 100 includes integrated front and rear displays 130A-130B which can both incorporate tactile, touch screen interface 131A-131B that can receive user tactile/touch input. As a touch screen device, integrated displays 130A-130B allow a user to provide input to or to control communication device 100 by touching features within the user interface presented on integrated displays 130A-130B. Tactile, touch screen interfaces 131A-131B can be utilized as input devices. The touch screen interfaces 131A-131B can each include one or more virtual buttons, indicated generally as 114a and 114b. In one or more embodiments, when a user applies a finger on one of touch screen interfaces 131A-131B in the region demarked by the virtual button 114*a* and/or 114*b*, the touch of the region causes the processor 102 to execute code to implement a function associated with the virtual button. Some embodiments can include a display screen on the same surface of the electronic device as the first image capturing device and the second image capturing device. In one or more embodiments, the controller is configured to render image content from at least one of the first image capturing device or the second image capturing device. Accordingly, the display screen that is on the same surface as the first and second image capturing devices is convenient to use when taking self-photos. In some implementations, integrated display 130A is a primary display that is integrated into a front surface of communication device 100, while the higher quality ICDs are located on a rear surface with rear display 130B. The specific physical and functional characteristics of integrated displays 130A-130B, e.g., screen size, aspect ratio, supported resolution, image quality, video display rate, etc., can vary and are known to or accessible by the processor 102.

Communication device 100 also includes a physical interface 165*a*. Physical interface 165*a* of communication device 100 can serve as a data port and can be coupled to charging circuitry 135 and device battery 143 to enable recharging of device battery 143.

Communication device 100 can further include microphone 108, one or more output devices such as speakers 144, and one or more input buttons 107*a*-107*n*. Microphone 108 can also be referred to as an audio input device. In some embodiments, microphone 108 may be used for identifying a user via voiceprint, voice recognition, and/or other suitable techniques. Input buttons 107*a*-107*n* may provide controls for volume, power, and ICDs 132, 133. Additionally, communication device 100 can include input sensors 109 (e.g., sensors enabling gesture detection by a user).

Communication device 100 further includes haptic touch controls 145, vibration device 146, fingerprint/biometric sensor 147, global positioning system (GPS) device 160, and motion sensor(s) 162. Vibration device 146 can cause communication device 100 to vibrate or shake when activated. Vibration device 146 can be activated during an incoming call or message in order to provide an alert or notification to a user of communication device 100. According to one aspect of the disclosure, integrated displays 130A and 130B, speakers 144, and vibration device 146 can generally and collectively be referred to as output devices.

Biometric sensor 147 can be used to read/receive biometric data, such as fingerprints, to identify or authenticate a user, and in some embodiments, the biometric sensor 147 can supplement an ICD (camera) for user detection/identification.

GPS device 160 can provide time data and location data about the physical location of communication device 100 using geospatial input received from GPS satellites. In one or more embodiments, the physical location of the communication device 100 is compared with the physical location of remote communication device 177. In one or more embodiments, remote communication device 177 includes components similar to those shown in communication device 100, including, but not limited to, the GPS device 160. The remote communication device 177 may transmit the physical location of remote communication device 177 to communication device 100 via wireless communication network 137. The communication device 100 then can compute a distance between communication device 100 and remote communication device 177 based on the location of both devices. In one or more embodiments, the location information may be transmitted as a tuple of information that includes a longitude-latitude pair. Motion sensor(s) 162 can include one or more accelerometers 163 and gyroscope 164. Motion sensor(s) 162 can detect movement of communication device 100 and provide motion data to processor 102 indicating the spatial orientation and movement of communication device 100. Accelerometers 163 measure linear acceleration of movement of communication device 100 in multiple axes (X, Y and Z). Gyroscope 164 measures rotation or angular rotational velocity of communication device 100. Communication device 100 further includes a housing 190 that is external to and contains/protects the components internal to communication device 100.

Communication device 100 further includes wireless communication subsystem (WCS) 142, which can represent one or more front end devices (not shown) that are each coupled to one or more antennas 148. In one or more embodiments, WCS 142 can include a communication module with one or more baseband processors or digital signal processors, one or more modems, and a radio frequency (RF) front end having one or more transmitters and one or more receivers. WCS 142 and antennas 148 allow communication device 100 to communicate wirelessly with a wireless communication network 137 via transmissions of communication signals to and from network communication devices, such as base stations or cellular nodes, of wireless communication network 137. Wireless communication network 137 further allows communication device 100 to wirelessly communicate with remote communication device 177, which can be similarly connected to wireless communication network 137. In one or more embodiments, wireless communication network 137 can be interconnected with a wide area network that can include one or more devices that support exchange of audio and video messages, data, and/or other communication between communication device 100 and remote communication device 177.

Wireless interface 165*b* can be a short-range wireless communication component providing Bluetooth, near field communication (NFC), and/or wireless fidelity (Wi-Fi) connections. In one embodiment, communication device 100 can receive Internet or Wi-Fi based calls via wireless interface 165*b*. In one embodiment, communication device 100 can communicate wirelessly with external wireless transceiver device 166, such as a WiFi router or BT transceiver, via wireless interface 165*b*. In an embodiment, WCS 142, antenna(s) 148, and wireless interface 165*b* collectively provide communication interface(s) of communication device 100.

Figure 2:
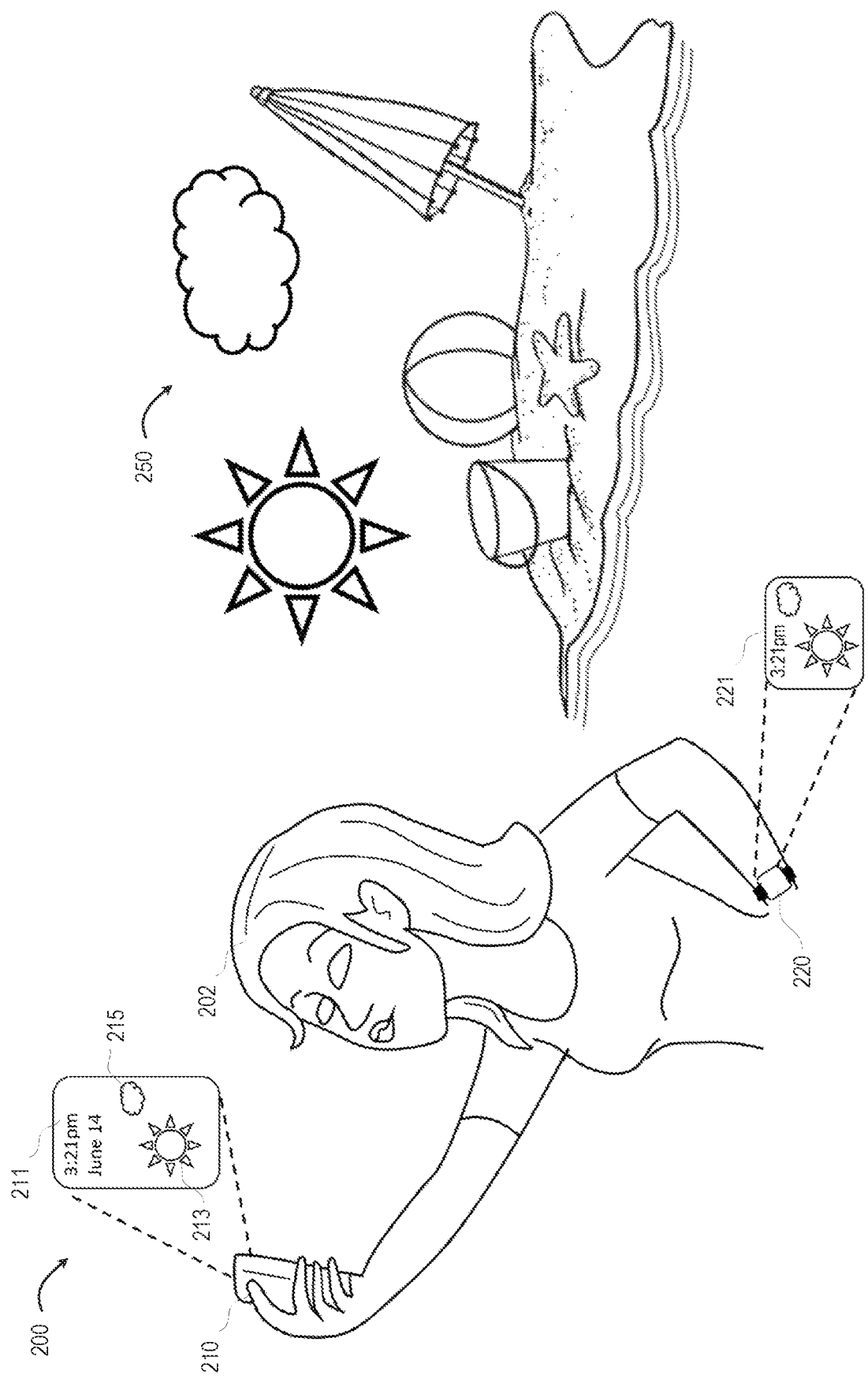
FIG. 2 is a diagram illustrating device customization based on image content, according to one or more embodiments.

FIG. 2 is a diagram 200 illustrating device customization based on image content, according to one or more embodiments. A user 202 is holding a first electronic device, which is smartphone 210, while wearing a second electronic device, which is smartwatch 220. Device 210 may be an implementation of communication device 100 (FIG. 1) having the same or similar components and providing the same or similar functions as communication device 100. The user 202 is taking a self-photo using one or more of the image capturing devices within smartphone 210. Based on information in the image, such as background elements 250 that appear in the self-photo, a sun and beach user context is identified. This causes a controller (processor) within the smartphone 210 to render a customization display theme that includes sun-themed elements, such as an image of the sun 213 and a cloud 215. The controller, in response to detecting an associated (e.g., paired) second electronic device, such as smartwatch 220, can also transmit a customization display theme to the second electronic device. As can be seen in FIG. 2, the customization display theme 211 is rendered on first electronic device 210, while a similar customization display theme 221 is rendered on second electronic device 220. Accordingly, in embodiments, the customization display theme may be automatically loaded on a smartphone and associated smartwatch, based on a user context and/or device context that is obtained from image data and/or environmental data.

One or more embodiments can include, transmitting instructions to the second electronic device to cause the second electronic device to load a second customization display theme on the second electronic device, wherein the second customization display theme includes one or more theme elements that correspond to the customization display theme of the electronic device. One or more embodiments can include, transmitting, via a communication interface of the electronic device, instructions to a second electronic device to cause the second electronic device to load a second customization display theme on a display of the second electronic device, wherein the second customization display theme is selected based on the device context.

Figure 3:
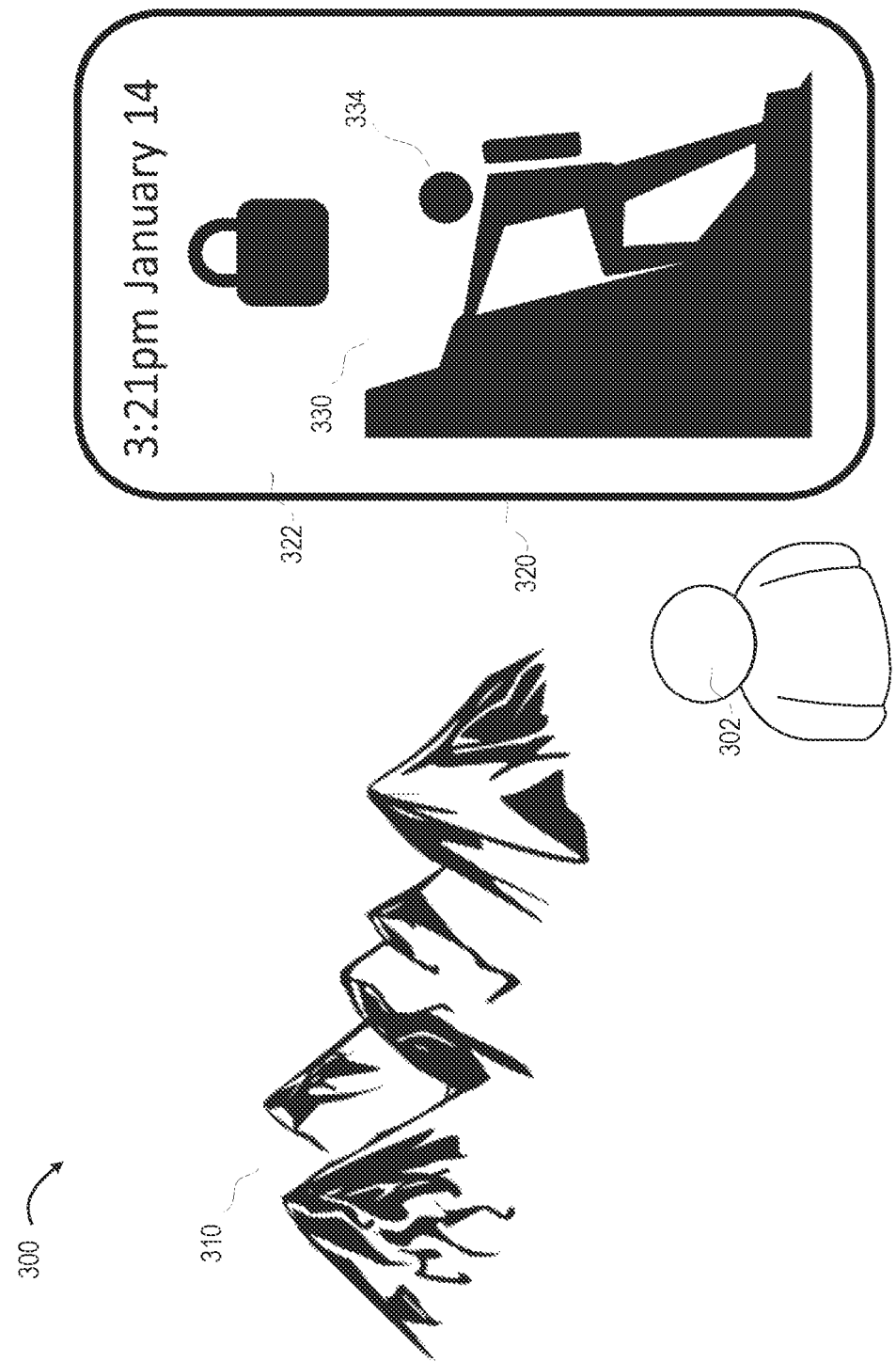
FIG. 3 is a diagram illustrating device customization based on geographical location, according to one or more embodiments.

FIG. 3 is a diagram 300 illustrating device customization based on geographical location, according to one or more embodiments. An electronic device 320 associated with a user 302 is at a geographical location 310. Device 320 may be an implementation of communication device 100 (FIG. 1) having the same or similar components and providing the same or similar functions as communication device 100. In one or more embodiments, based on the geographical location 310, and/or conditions associated with geographical location 310, a customization display theme 330 is rendered on the display 322 of electronic device 320. In the example of FIG. 3, the customization display theme 330 includes an image of a person 334 mountain climbing. In one or more embodiments, a customization display theme including an image of a mountain climber may be rendered on the display 322 in response to determining that a geographical location 310 is in a mountainous region. In one or more embodiments, the geographical location can be obtained via a GPS in device 320, similar to as shown at 160 in FIG. 1. Other techniques for geographical location determination are possible in disclosed embodiments, including, but not limited to, IP address geolocation. IP address geolocation is the process of determining the physical location of an IP address on the Internet. IP addresses are allocated to organizations (such as Internet Service Providers) by regional Internet registries (RIRs) and/or other governing bodies. These organizations then assign IP addresses to their users or subscribers. Various companies and organizations maintain databases that associate IP addresses with geographical information. These databases can be created through a combination of methods, including data provided by RIRs, public records, user-contributed data, and proprietary techniques. While IP (Internet Protocol) address geolocation may not pinpoint the exact physical location of specific electronic device, it can provide a general location or vicinity that can be used for determining an appropriate customization display theme in accordance with one or more embodiments. One or more embodiments can include identifying a current geographical location for the electronic device; and setting the device context based on the current geographical location. In one or more embodiments, loading the customization display theme further comprises rendering at least one of a background image and a lock screen image on a display of the electronic device, selected based on the device context.

Figure 4:
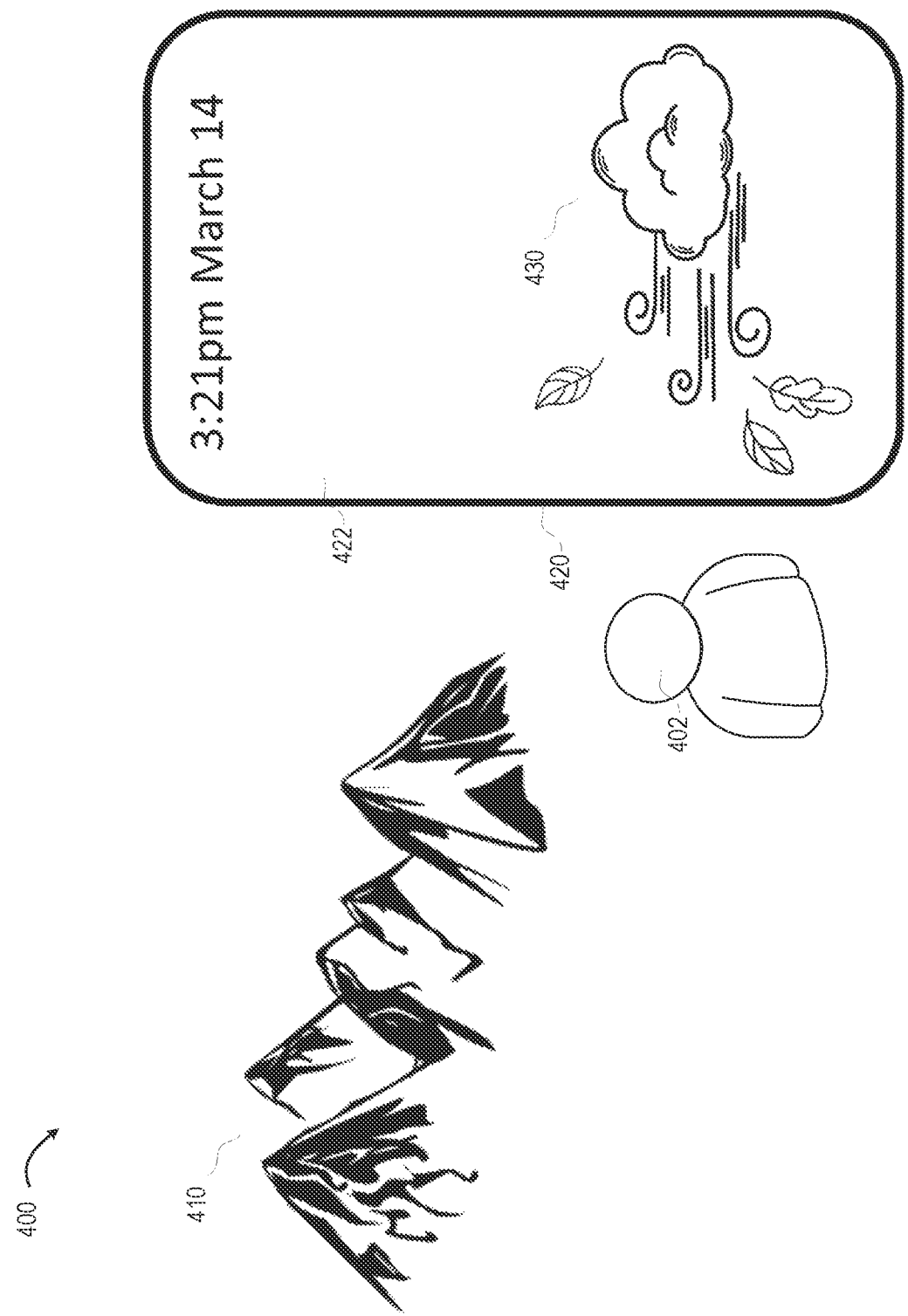
FIG. 4 is a diagram illustrating device customization based on a current meteorological condition, according to one or more embodiments.

FIG. 4 is a diagram 400 illustrating device customization based on a current meteorological condition, according to one or more embodiments. An electronic device 420 associated with a user 402 is at a geographical location 410. Device 420 may be an implementation of communication device 100 (FIG. 1) having the same or similar components and providing the same or similar functions as communication device 100. In one or more embodiments, based on a current meteorological condition, a device context is determined. Based on the device context, a customization display theme is rendered on the display 422 of device 420. In FIG. 4, a user 402, along with his/her electronic device 420, are at a geographical location 410. In one or more embodiments, the device 420 determines a geographical location via onboard GPS, IP address geolocation, and/or other suitable techniques. The device 420 retrieves current meteorological conditions for the current geographical location of the device. Based on the current meteorological conditions, a customization display theme is loaded/rendered on the display 422 of the electronic device. In the example of FIG. 4, the meteorological conditions at geographical location 410 include wind. Based on the wind speed exceeding a predetermined threshold (e.g., a wind speed greater than 30 kilometers per hour), an image 430 that indicates windiness is rendered. Embodiments can utilize other meteorological conditions for determining a customization display theme to render. Examples can include ambient outdoor air temperature. For example, a device can render an image of ice cream cones when the ambient outdoor air temperature exceeds 27 degrees Celsius, can render an image of a hot bowl of soup when the ambient outdoor air temperature falls below 5 degrees Celsius, and so on. These are merely examples, and other images and criteria can be used in disclosed embodiments. One or more embodiments can include receiving a current meteorological condition for a current location of the electronic device; and setting the device context based on the current meteorological condition. In one or more embodiments, the current meteorological condition includes one or more of an outdoor temperature and a wind speed.

Figure 5:
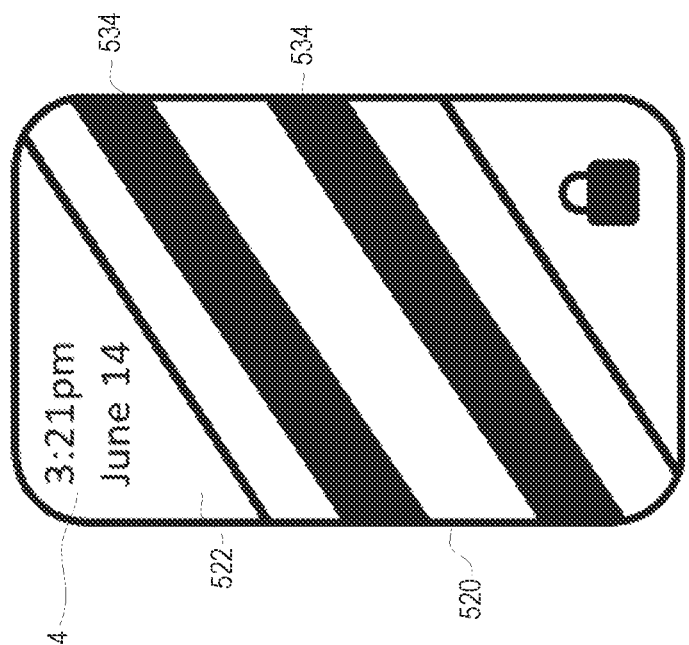
FIG. 5 is a diagram illustrating an example of device customization based on identified apparel, according to one or more embodiments.
Figure 5:
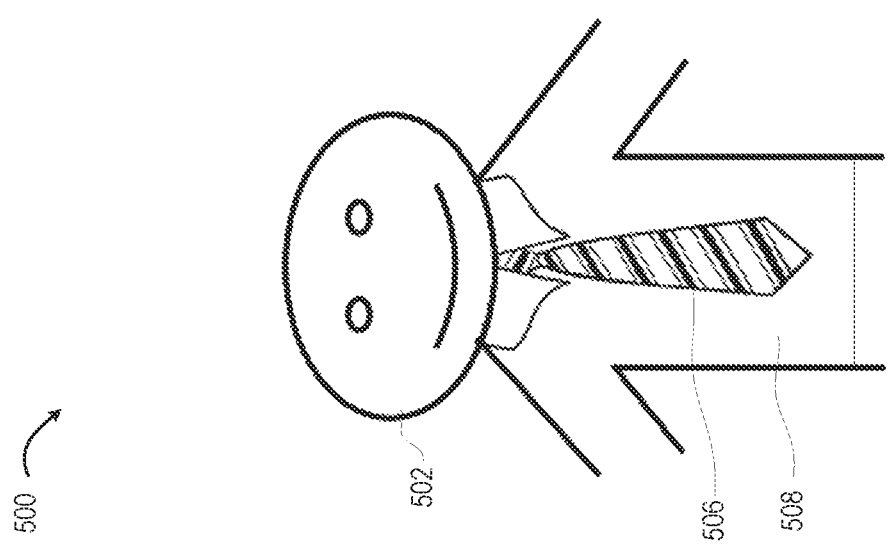

FIG. 5 is a diagram 500 illustrating an example of device customization based on identified apparel, according to one or more embodiments. A user 502 is wearing apparel 508 that includes a necktie 506. The necktie 506 includes a striped pattern of various shades and/or colors. The user 502 takes a self-photo with his electronic device 520, similar to as shown by user 202 with electronic device 210 in FIG. 2. Device 520 may be an implementation of communication device 100 (FIG. 1) having the same or similar components and providing the same or similar functions as communication device 100. The image content of the self-photo is analyzed to determine the attire. The analysis can be performed on the device 520. Alternatively, the image content can be transmitted to a remote server for analysis, and results can be provided to the electronic device 520. The results can include identification of colors and/or patterns. The results can include an image that the electronic device 520 can use as a background image. The analysis can include machine learning. The analysis can be based on one or more image classifiers.

Figure 6:
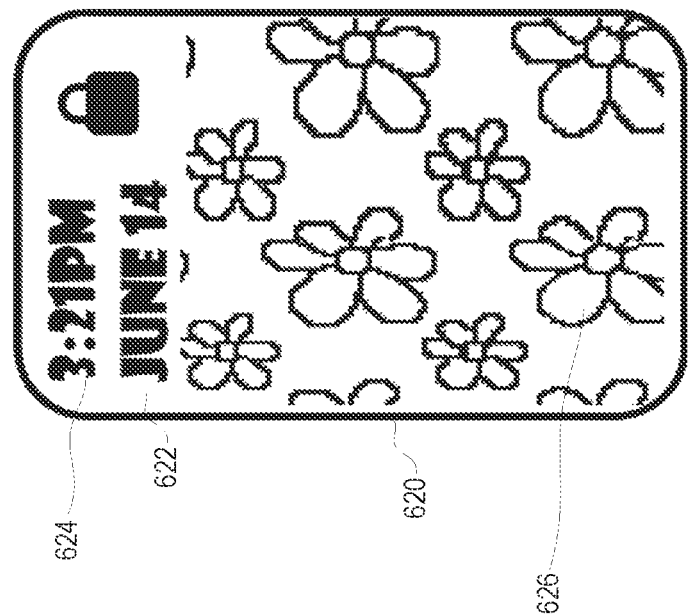
FIG. 6 is a diagram illustrating another example of device customization based on identified apparel, according to one or more embodiments.
Figure 6:
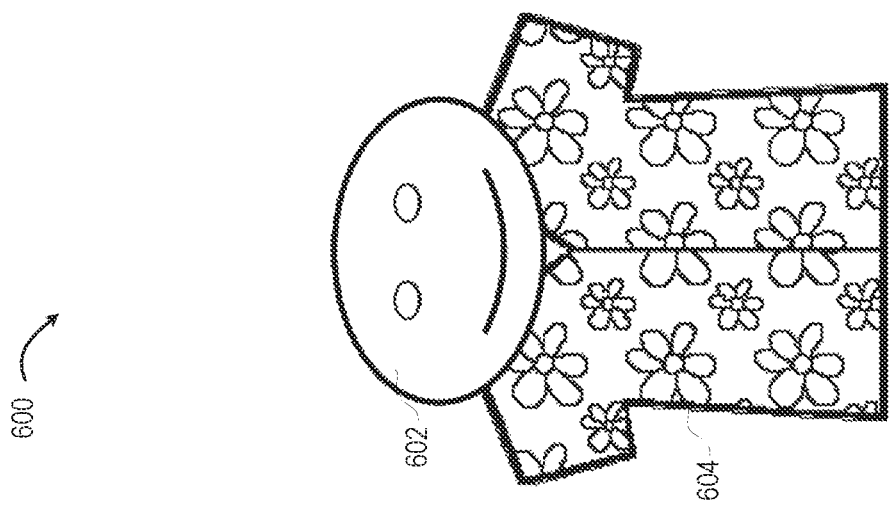

In the example of FIG. 5, the attire analysis includes identification of necktie 506, which causes a controller (processor) within electronic device 520 to render font 524, which is a plain (non-serif) font for the date and time on display 522. Additionally, a lock screen image includes a striped pattern including stripes, indicated at 534, where the stripe angle, pattern, and/or color matches or resembles the pattern of the necktie 506. This gives an appearance that the device 520 'goes with' the necktie 506. This enables the user 502 to use his electronic device 520 as a fashion accessory for business functions/purposes, as well as using it for the purposes of communication and/or other device functions. Embodiments can include identifying apparel worn by the user; and rendering an image corresponding to the identified apparel on the electronic display. Embodiments can include identifying a color within the apparel worn by the user; and wherein rendering the image comprises rendering a background image that includes a similar color to the color of the identified apparel FIG. 6 is a diagram 600 illustrating another example of device customization based on identified apparel, according to one or more embodiments. A user 602 is wearing apparel that includes a shirt 604. The shirt 604 includes a floral pattern of various shades and/or colors. The user 602 takes a self-photo with his electronic device 620, similar to as shown by user 202 with electronic device 210 in FIG. 2. Device 620 may be an implementation of communication device 100 (FIG. 1) having the same or similar components and providing the same or similar functions as communication device 100. The image content of the self-photo is analyzed to determine the attire. The analysis can be performed on the device 620. Alternatively, the image content can be transmitted to a remote server for analysis, and results can be provided to the electronic device 620. The results can include identification of colors and/or patterns. The results can include an image that the electronic device 620 can use as a background image. The analysis can include machine learning. The analysis can be based on one or more image classifiers.

In the example of FIG. 6, the attire analysis includes identification of shirt 604, which causes a controller (processor) within electronic device 620 to render font 624, which is a casual (non-business) font for the date and time on display 622. Additionally, a lock screen image includes a floral pattern including multiple flowers, indicated generally at 626, where the flower pattern, and/or color matches or resembles the pattern of the shirt 604. This gives an appearance that the device 620 'goes with' the shirt 604. thereby enabling the user 602 to use his electronic device 620 as a fashion accessory for casual purposes/functions, as well as using it for the purposes of communication and/or other device functions.

Figure 7:
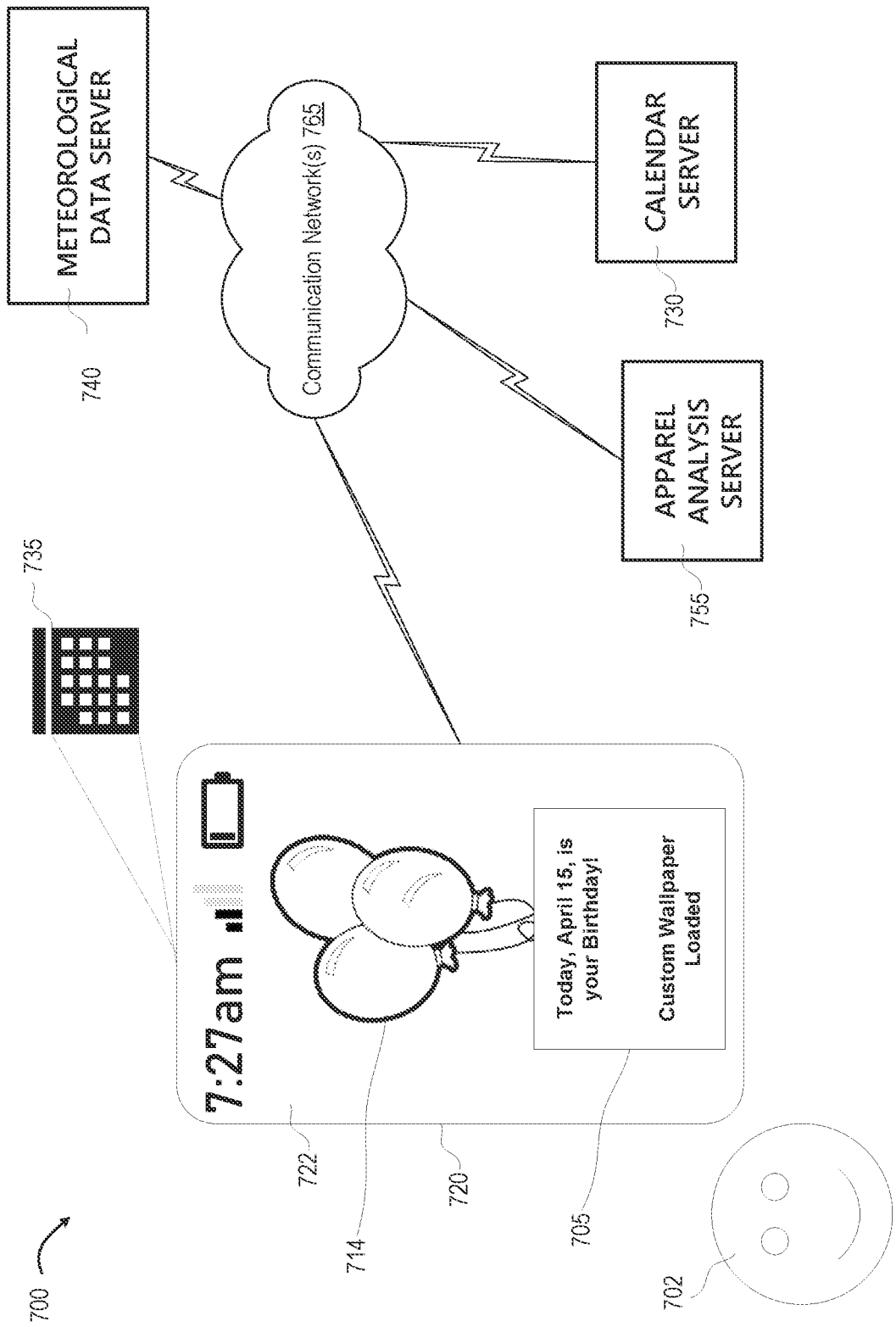
FIG. 7 is a diagram illustrating device customization based on a calendar event, according to one or more embodiments.

FIG. 7 is a diagram 700 illustrating device customization based on a calendar event, according to one or more embodiments. A user 702 has an associated electronic device 720. Device 720 may be an implementation of communication device 100 (FIG. 1) having the same or similar components and providing the same or similar functions as communication device 100. The device 720 communicates with a calendar server 730 via communication network(s) 765. Communication network(s) 765 can include one or more wired and/or wireless communication networks, including the Internet. The calendar server 730 can include one or more computers, virtual machines, containerized applications, and so on. The calendar server 730 can store calendar information in a format such as RFC 5545 (Internet Calendaring and Scheduling Core Object Specification), and/or other suitable format. The calendar server 730 can store holiday information, including international, national, regional, and/or local holiday information. Additionally, the calendar server 730 can store personal event information that pertains to user 702, such as birthdays, anniversaries, and the like.

In the diagram 700, the display 722 of device 720 renders a customization display theme that includes image 714 of balloons, based on a calendar event of the date of April 15, since it is the birthday of the user 702, based on information obtained from calendar server 730. Optionally, the device 720 can also render a notification 705 indicating the loading of a customization display theme. In one or more embodiments, instead of, or in addition to, operating on calendar events stored in calendar server 730, the device 720 may store a local calendar 735 that is internally stored within the system memory (120 of FIG. 1) of the device 720. This enables operations based on calendar events without the need for network connectivity. This can be useful when the device 720 is in a remote location without cellular or WiFi connectivity.

Embodiments can include other servers instead of, or in addition to, calendar server 730. One or more embodiments can include a meteorological data server 740. In embodiments, device 720 sends a query to meteorological data server 740 via communication network(s) 765. The query can include a current geographical location of the device 720. Based on the current geographical location, the meteorological data server 740 returns current weather conditions for that location. Based on the current weather conditions, a corresponding customization display theme can be loaded/rendered on the display 722 of the device 720. In one or more embodiments, obtaining context data comprises obtaining, from a calendar system, a calendar event associated with the electronic device.

One or more embodiments can include an apparel analysis server 755. In embodiments, device 720 sends image content, such as a self-photo, to apparel analysis server 755 via communication network(s) 765. The apparel analysis server 755 can analyze the image content using machine learning techniques, in order to identify patterns, colors, styles, and so on. Based on the image analysis, the apparel analysis server 755 can return images for use in a customization display theme, and/or text describing a corresponding customization display theme. The text can include a font type, font size, font style, and so on. Based on the identification of colors, patterns, style, and/or other factors, a corresponding customization display theme can be loaded/rendered on the display 722 of the device 720.

Figure 8A:
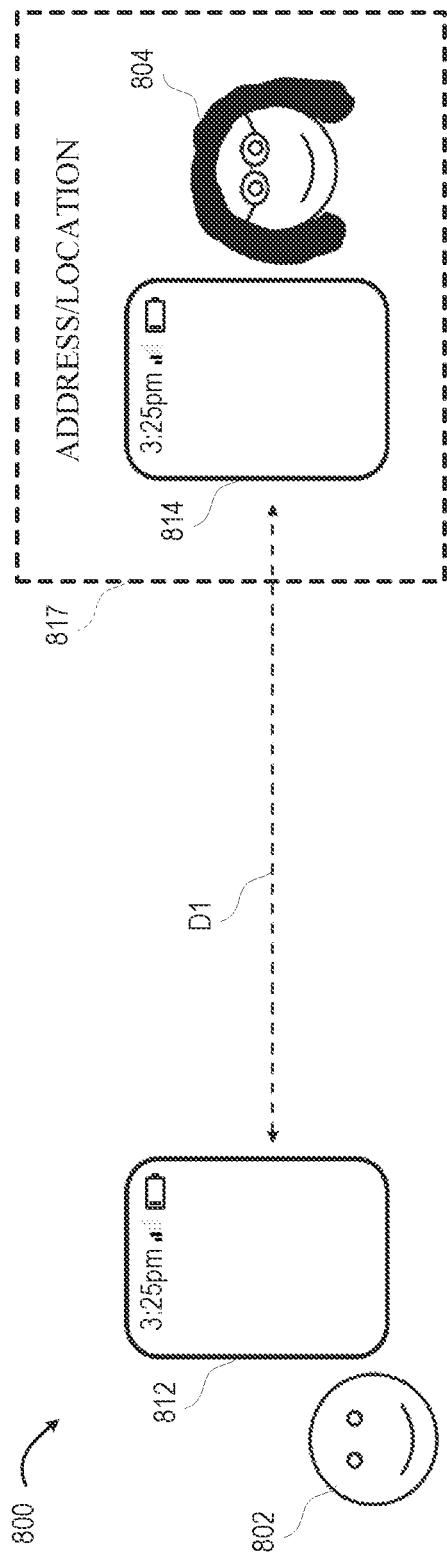
FIG. 8A and FIG. 8B show diagrams illustrating device customization based on a distance between two electronic devices, according to one or more embodiments.
Figure 8B:
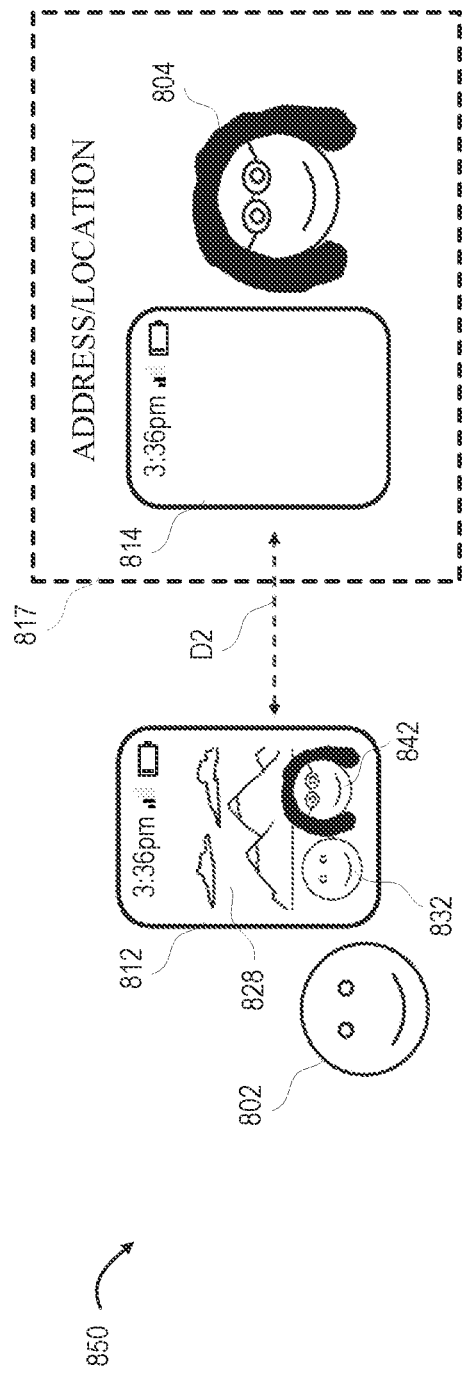

FIG. 8A and FIG. 8B show diagrams illustrating device customization based on a distance between two electronic devices, according to one or more embodiments. Referring to FIG. 8A, it includes diagram 800 which includes a first user 802 and a second user 804. First user 802 has an associated electronic device 812. Second user 804 has an associated electronic device 814 at a given address or location, indicated by reference 817. Device 812 and device 814 may each be an implementation of communication device 100 (FIG. 1) having the same or similar components and providing the same or similar functions as communication device 100. Device 812 is separated from device 814 by a distance D1. Now referring to FIG. 8B, it includes diagram 850 in which device 812 is separated from device 814 by a distance D2, where D2 is less than D1. Based on the proximity of device 812 to device 814, a customization display theme can be loaded on the display 828 of device 812, where the customization display theme includes an image that includes an image 842 of user 804, and may optionally include an image 832 of user 802. As an example use case, when a user visits his sister, the customization display theme can include an image of the user's sister, or an image of the user and his sister together, which is rendered automatically when the electronic device of the user is within a predetermined distance of the second electronic device, which is associated with the sister of the user. One or more embodiments can include, determining that a distance between the electronic device and the second electronic device is less than a predetermined threshold distance; determining the device context based on a user identifier associated with the second electronic device; obtaining an image associated with the user identifier, and rendering the image as a background image on the display of the electronic device in response to the distance being less than a predetermined threshold distance.

As an alternate implementation to the above use case, the determination of the distance to another person, such as the device user's sister, is based on a known physical address or location of the sister, without requiring any location data of the sister's phone or other electronic device. Similarly to the above use case, when the user visits his sister, the customization display theme can include an image of the user's sister, or an image of the user and his sister together, which is rendered automatically when the electronic device of the user is within a predetermined distance of the sister's home or office or other stored location within the user's phone that is associated with the user's sister. In one or more embodiments, the user's device 812 can utilized GPS location tracking of the user's device, relative to the known location, or a navigation tool to determine when the user's device 812 is within the pre-established threshold distance from the stored address/location or when the user's device 812 is approaching the stored address/location. With a navigational tool embodiment, the address can be inputted by the user. The one or more embodiments can then include: determining the device context based on an identification of the one or more contacts (e.g., the user's sister); obtaining an image associated with the one or more contacts; and rendering the image as a background image on the display of the electronic device in response to the distance being less than the predetermined threshold distance.

Figure 9:
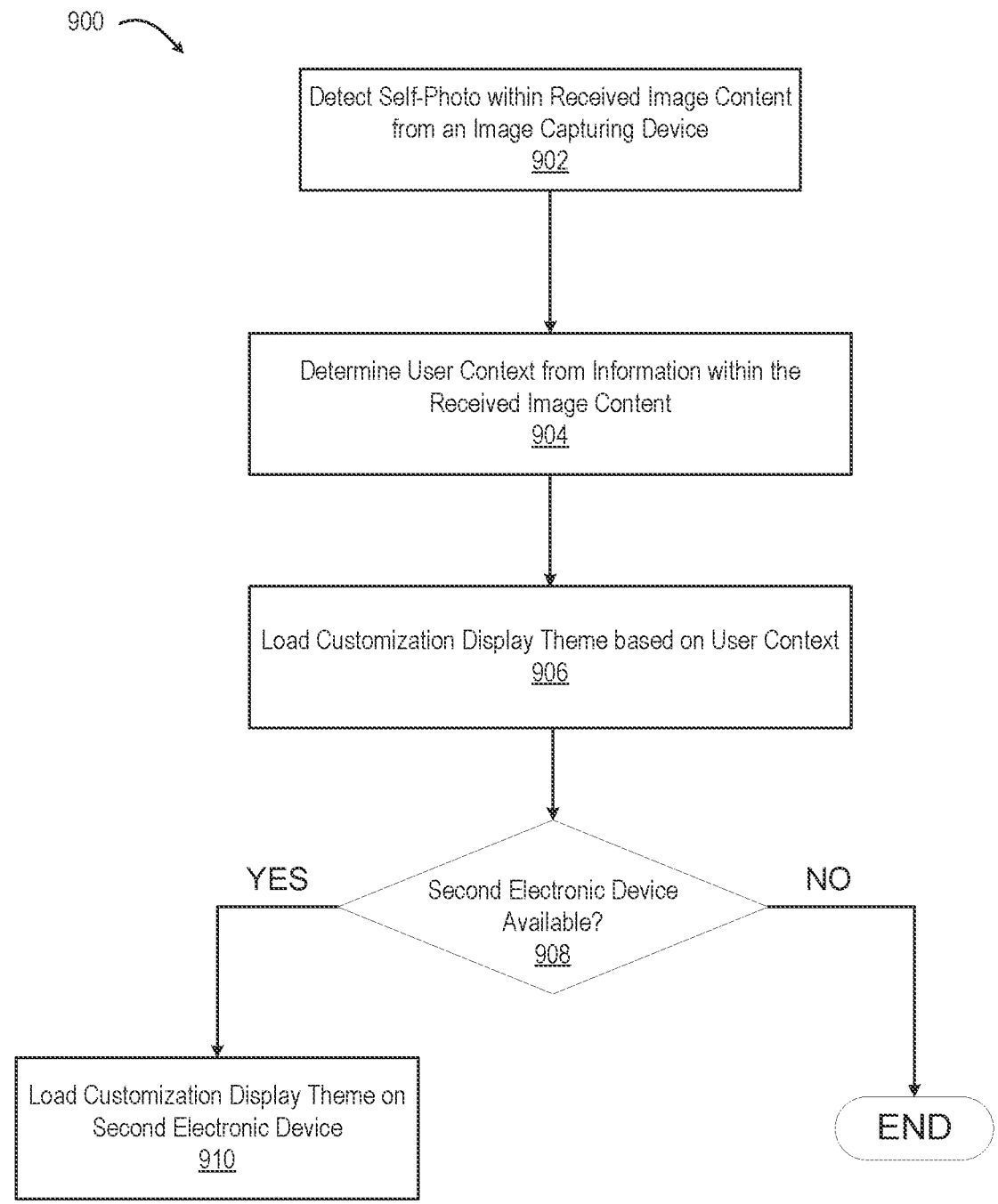
FIG. 9 depicts a flowchart of a method by which an electronic device enables customization based on received image content, according to one or more embodiments.
Figure 10:
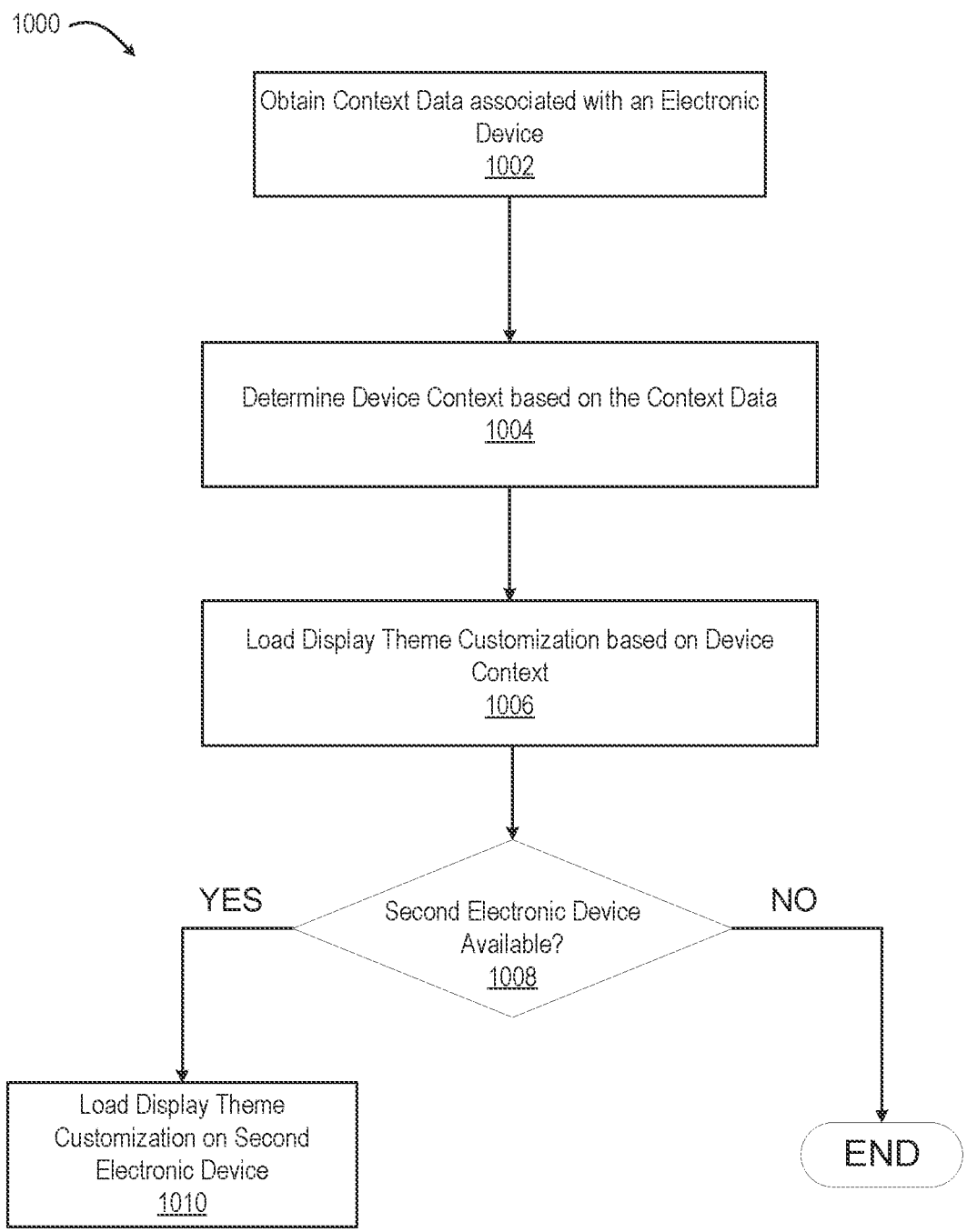
FIG. 10 depicts a flowchart of a method by which an electronic device enables customization based on a device context, according to one or more embodiments.
Figure 11:
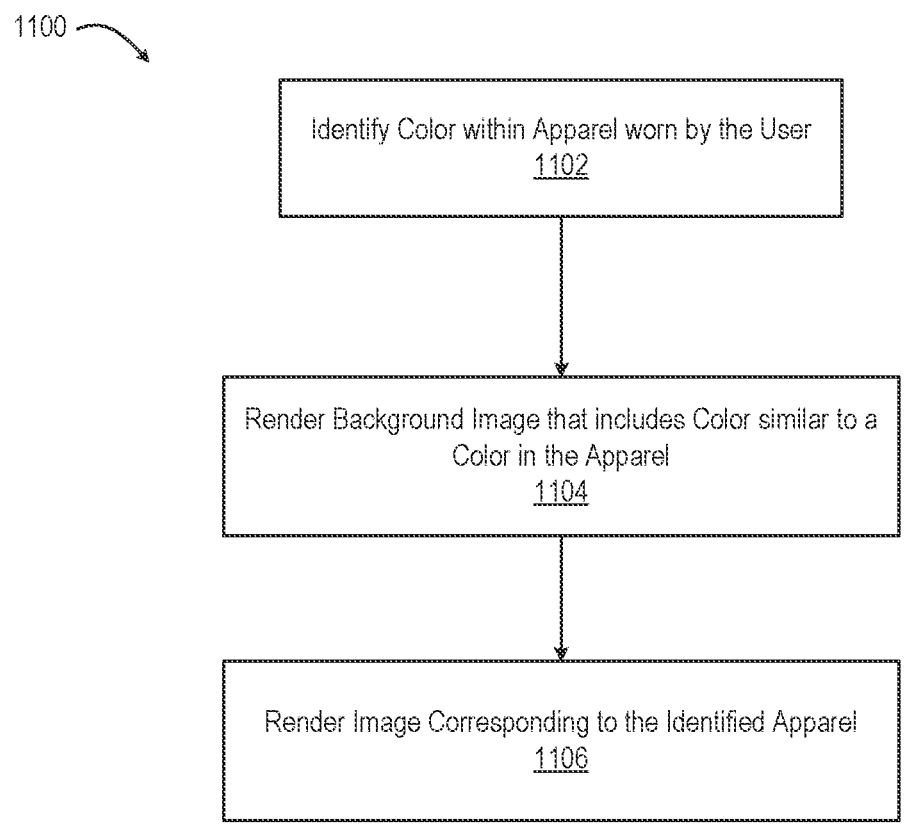
FIG. 11 depicts a flowchart of a method by which an electronic device enables customization based on identified apparel, according to one or more embodiments.
Figure 12:
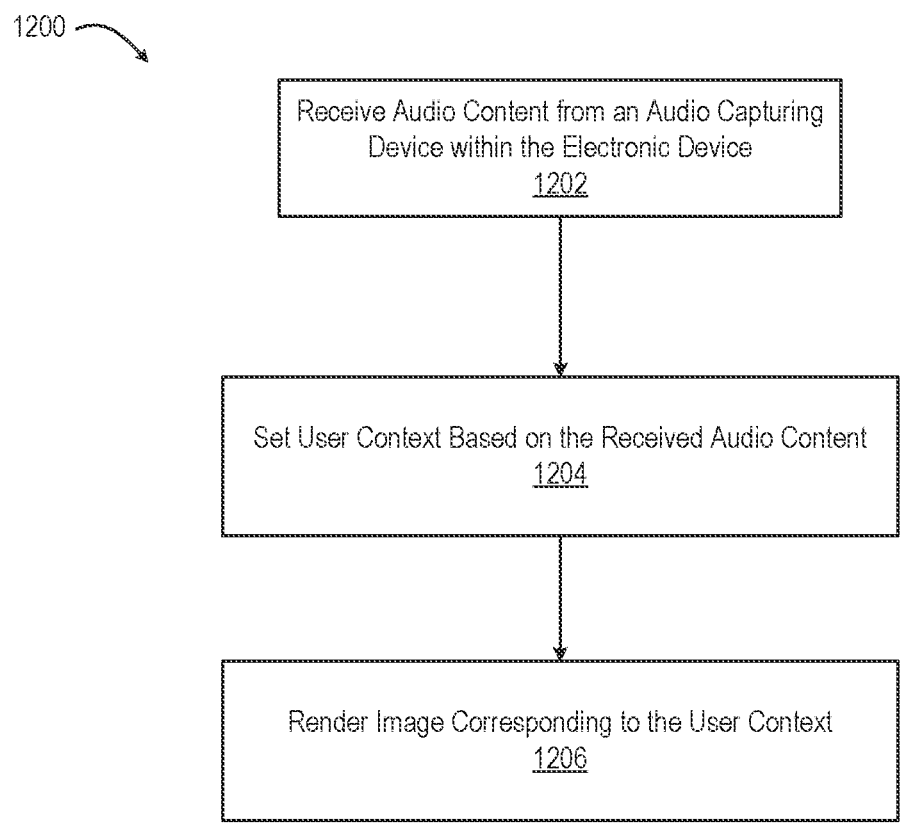
FIG. 12 depicts a flowchart of a method by which an electronic device enables customization based on received audio content, according to one or more embodiments.
Figure 13:
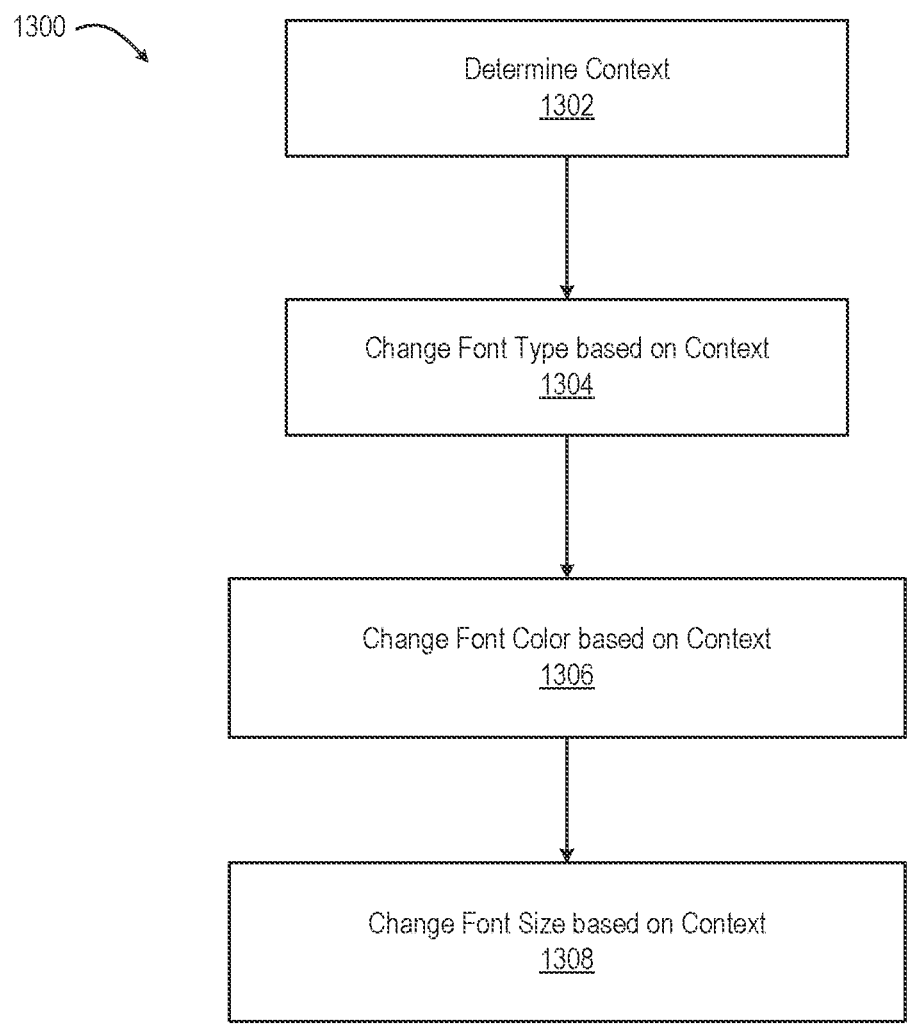
FIG. 13 depicts a flowchart of a method by which an electronic device enables customization that includes font changes, according to one or more embodiments.
Figure 14:
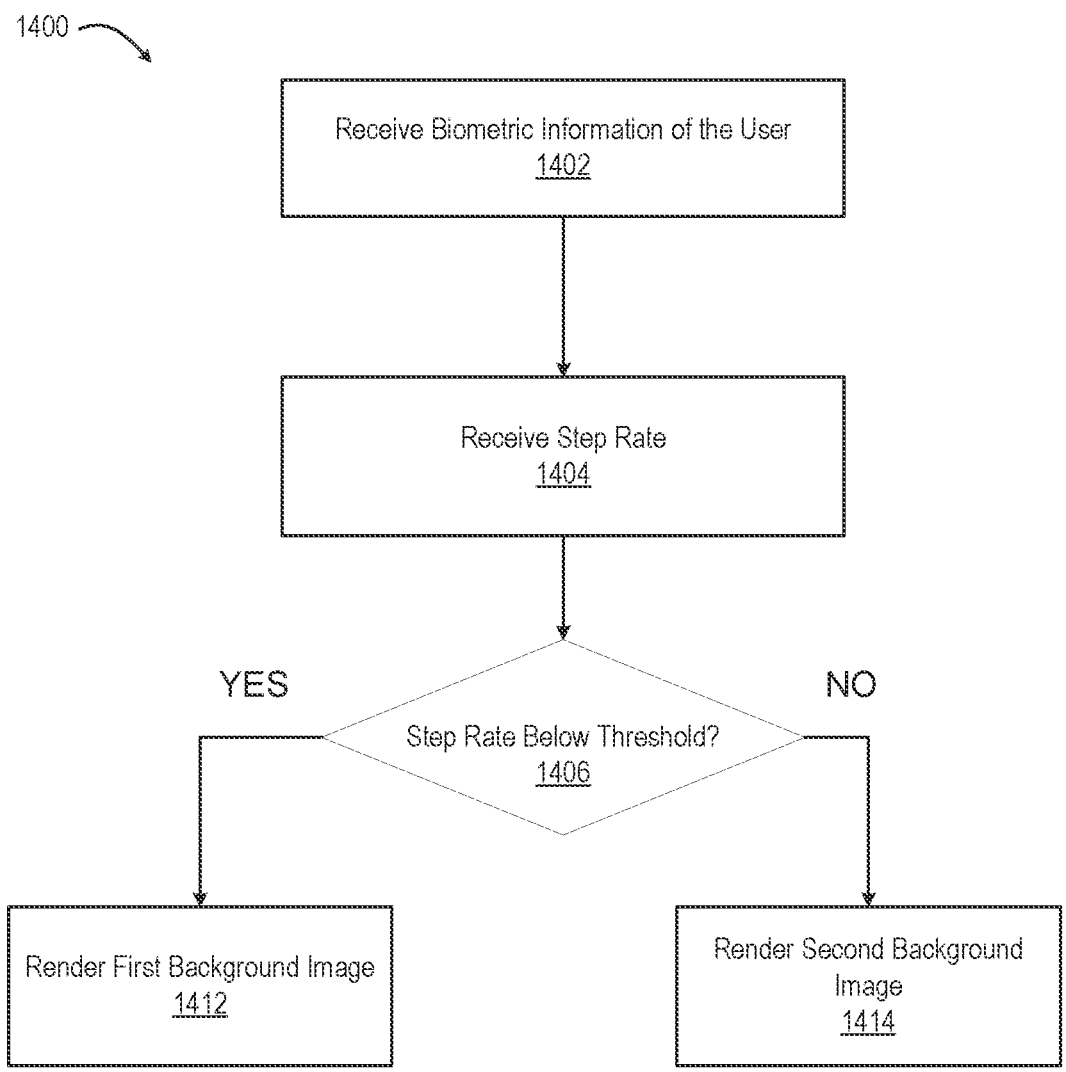
FIG. 14 depicts a flowchart of a method by which an electronic device enables customization based on received biometric information including a step rate, according to one or more embodiments.
Figure 15:
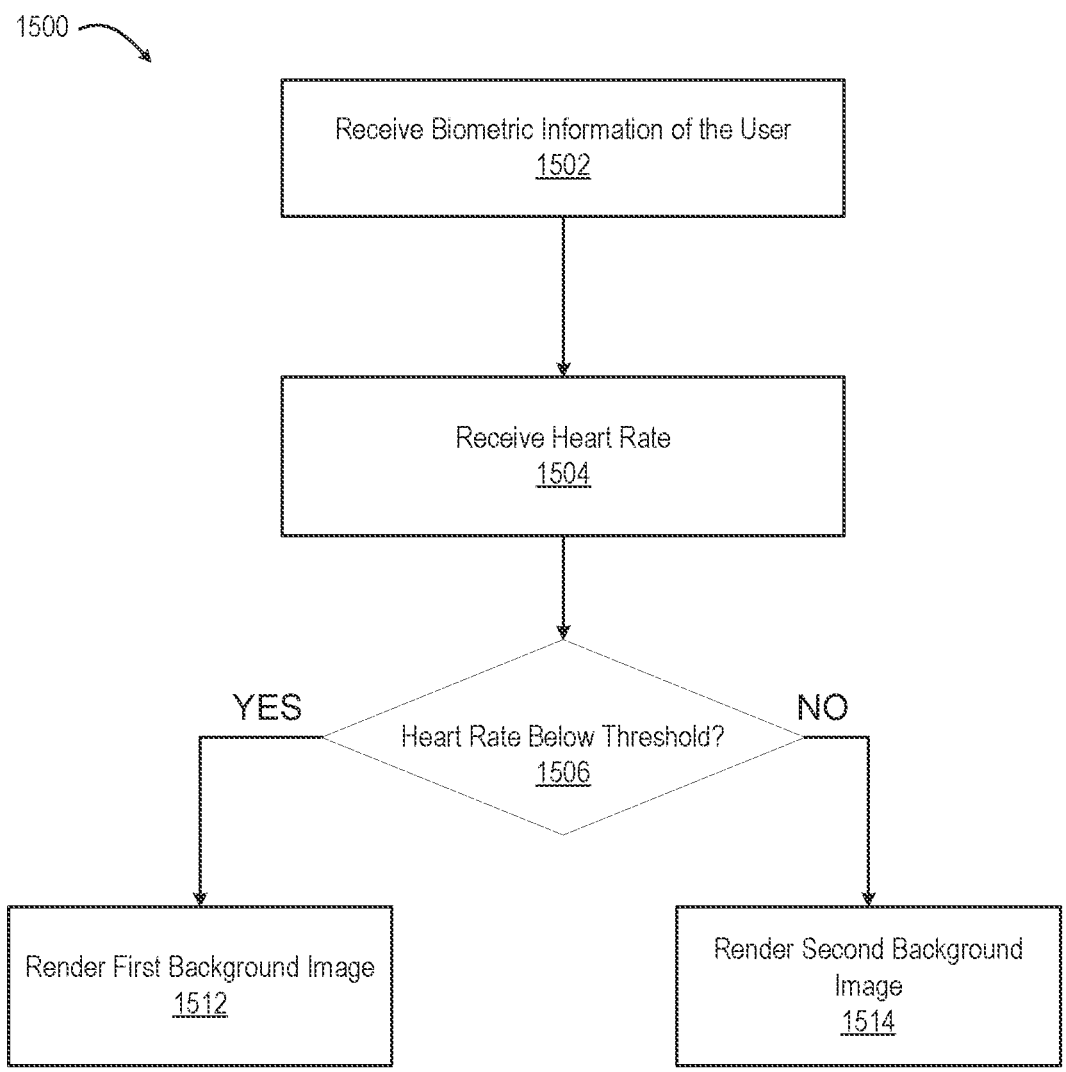
FIG. 15 depicts a flowchart of a method by which an electronic device enables customization based on received biometric information including a received heart rate, according to one or more embodiments.
Figure 16:
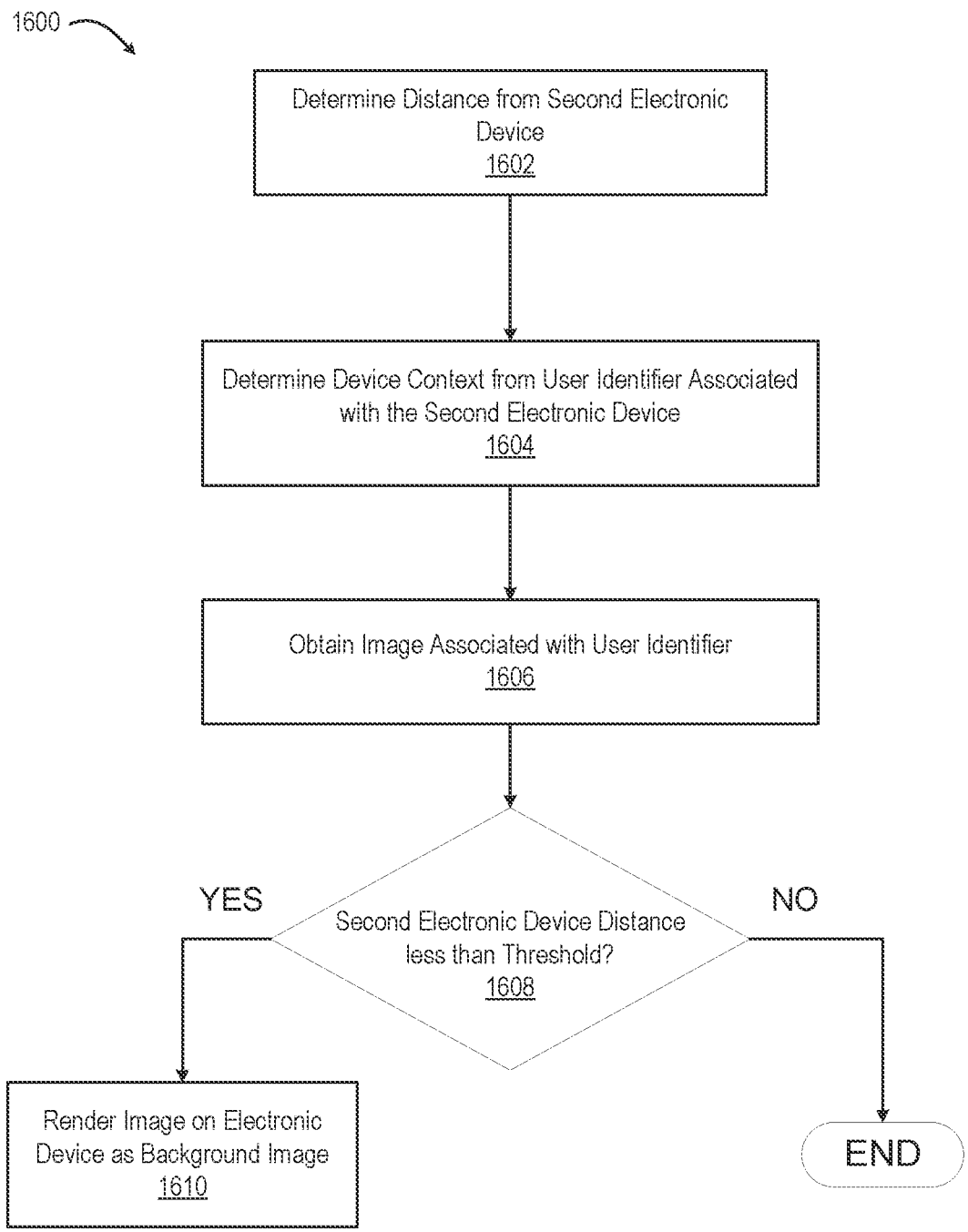
FIG. 16 depicts a flowchart of a method by which an electronic device enables customization based on distance from a second electronic device, according to one or more embodiments.

Referring now to the flow charts, FIG. 9 depicts a flowchart of a method 900 by which an electronic device enables customization based on received image content, according to one or more embodiments. FIG. 10 depicts a flowchart of a method 1000 by which an electronic device enables customization based on a device context, according to one or more embodiments. FIG. 11 depicts a flowchart of a method 1100 by which an electronic device enables customization based on identified apparel, according to one or more embodiments. FIG. 12 depicts a flowchart of a method 1200 by which an electronic device enables customization based on received audio content, according to one or more embodiments. FIG. 13 depicts a flowchart of a method 1300 by which an electronic device enables customization that includes font changes, according to one or more embodiments. FIG. 14 depicts a flowchart of a method 1400 by which an electronic device enables customization based on received biometric information including a step rate, according to one or more embodiments. FIG. 15 depicts a flowchart of a method 1500 by which an electronic device enables customization based on received biometric information including a heart rate, according to one or more embodiments. FIG. 16 depicts a flowchart of a method 1600 by which an electronic device enables customization based on distance from a second electronic device, according to one or more embodiments. The descriptions of methods in FIGS. 9-16 are provided with general reference to the specific components illustrated within the preceding FIGS. 1-8B. Specific components referenced in FIGS. 9-16 may be identical or similar to components of the same name used in describing preceding FIGS. 1-8B. In one or more embodiments, processor 102 (FIG. 1) configures communication device 100 (FIG. 1) to provide the described functionality of the methods depicted in FIGS. 9-16 by executing program code for one or more modules or applications provided within system memory 120 of communication device 100.

FIG. 9 depicts a flowchart of a method 900 by which an electronic device enables customization based on received image content, according to one or more embodiments. The method starts at block 902 where a self-photo is detected within received image content from an image capturing device. In one or more embodiments, the image capturing device can include a front-facing or rear-facing camera of the electronic device. The method continues to block 904, where a user context is determined from information within the received image content. The user context can include a style, such as business, casual, party, active, etc. The user context can include an activity, such as golf, tennis, dancing, boating, etc. The user context can be based on apparel, biometric information, received audio content, and/or other criteria.

The method continues to block 906 where a customization display theme is loaded on the electronic device based on the user context. The customization display theme can include images. The images can be photographs, illustrations, animated GIFs, and so on. The images can be included as wallpapers for a background image for a home screen and/or lock screen of an electronic device. The customization display theme can include font information. The font information can include a font type, size, and/or style. The customization display theme can include a user interface theme. The menu theme can include style and/or placement of user interface elements such as dropdown menus, radio buttons, checkboxes, and the like. Other customization display theme elements are possible in disclosed embodiments.

The method continues to block 908, where a check is made to determine if a second electronic device is available. The availability criteria can include the electronic device detecting the presence of the second electronic device via wireless communication protocols, and/or being communicatively coupled to the second electronic device (e.g., via Bluetooth® pairing). If, at block 908, a second electronic device is not available, the method ends. If, at block 908, a second electronic device is available, the method continues to loading a customized display theme on the second electronic device 910. In one or more embodiments, the second electronic device can be a wearable computer such as a smartwatch, that is communicatively coupled to the electronic device via Bluetooth® or other suitable techniques. An example of this is illustrated in FIG. 2 where device 210 and device 220 each have a similar customized display theme rendered thereon. Accordingly, in disclosed embodiments, an electronic device such as a smartphone, and a second electronic device such as a smartwatch, can have a similar customization display theme to provide a cohesive fashion appearance for a user.

FIG. 10 depicts a flowchart of a method 1000 by which an electronic device enables customization based on a device context, according to one or more embodiments. Method 1000 starts with block 1002, where context data is obtained that is associated with one or more of a user and an electronic device. The context data can include various data associated with a user and/or a corresponding device. The context data can include geographical data, meteorological data, calendar event data, biometric data, and so on. The method 1000 continues to block 1004, where a device context is determined based on the context data. As an example, a device context of 'windy' can be determined based on meteorological data for a geographical location where an electronic device is located. When the meteorological data includes a wind speed that exceeds a predetermined threshold, a wind-themed customization display theme can be loaded on an electronic device, such as is depicted in FIG. 4.

The method 1000 continues to block 1006 where a customization display theme is loaded on the electronic device based on the user context. The customization display theme can include images. The images can be photographs, illustrations, animated GIFs, and so on. The images can be included as wallpapers for a background image for a home screen and/or lock screen of an electronic device. The customization display theme can include font information. The font information can include a font type, font color, font size, and/or font style. The customization display theme can include a user interface theme. The menu theme can include style and/or placement of user interface elements such as dropdown menus, radio buttons, checkboxes, and the like. Other customization display theme elements are possible in disclosed embodiments.

The method 1000 continues to block 1008, where a check is made to determine if a second electronic device is available. If, at block 1008, a second electronic device is not available, the method ends. If, at block 1008, a second electronic device is available, the method continues to loading a customized display theme on the second electronic device 1010. In one or more embodiments, the second electronic device can be a wearable computer such as a smartwatch, that is communicatively coupled to the electronic device via Bluetooth® or other suitable techniques. An example of this is illustrated in FIG. 2 where device 210 and device 220 each have a similar customized display theme rendered thereon. Accordingly, in disclosed embodiments, an electronic device such as a smartphone, and a second electronic device such as a smartwatch, can have a similar customization display theme to provide a cohesive fashion appearance for a user.

FIG. 11 depicts a flowchart of a method 1100 by which an electronic device enables customization based on identified apparel, according to one or more embodiments. Method 1100 starts at block 1102, where a color is identified within apparel worn by the user. In one or more embodiments, this occurs when image content from a self-photo is acquired by one or more image capturing devices (cameras) of the electronic device. In one or more embodiments, apparel is identified based on image analysis that can include machine learning techniques. In one or more embodiments, the apparel is identified as a region of pixels within image content, and the color is determined based on an RGB (red green blue) tuple of data for each pixel. In one or more embodiments, the RGB values of a group of pixels may be averaged in order to determine an overall color of apparel. The method 1100 then continues to block 1104, where the device renders a background image that includes a color similar to a color in the apparel. As an example, if the color red is detected in the apparel, then the background image may contain a similar shade of red. The method 1100 can further include rendering an image corresponding to the identified apparel at 1106. The image can be a background image. The image can correspond to the identified apparel based on color, pattern, and/or other design elements. An example of such an image is shown in FIG. 5 on device 520 where the rendered image includes a striped pattern that is similar to a pattern detected in the necktie 506. Accordingly, in disclosed embodiments, an electronic device such as a smartphone, can have a similar customization display theme based on the apparel being worn by the user, in order to provide a cohesive fashion appearance for a user.

FIG. 12 depicts a flowchart of a method 1200 by which an electronic device enables customization based on received audio content, according to one or more embodiments. The method starts with receiving audio content from an audio capturing device within the electronic device 1202. In one or more embodiments, the audio data can be received from an onboard microphone such as microphone 108 of communication device 100 as shown in FIG. 1. In one or more embodiments, the audio data can include music. In one or more embodiments, the device analyzes the audio data to determine the tempo of music. The method 1200 continues to block 1204, where the user context is set. The user context can be based on the tempo of the music. As an example, a fast tempo (e.g., 120 beats per minute or greater) can cause a controller (processor) within the electronic device to set a specific user context that causes loading of a specific customization display theme. In embodiments, determining the user context is further based on received audio content from an audio capturing device communicatively coupled to the at least one processor. The method 1200 continues with rendering an image corresponding to the user context at block 1206. In one or more embodiments, in response to the detected audio data, the electronic device renders a background image that includes an image of an artist that created the song, and/or other images associated with the tempo, genre, and/or other musical parameters that are detected.

In some embodiments, one or more of the font type, font color, and/or font size is changed as the result of loading a customization display theme. Examples of such font changes are shown in font 524 of FIG. 5 and font 624 of FIG. 6. FIG. 13 depicts a flowchart of a method 1300 by which an electronic device enables customization that includes font changes, according to one or more embodiments. The method 1300 starts at block 1302, where a context is determined. The context can be a device context or user context as previously described. The method 1300 continues to block 1304, where a font type is changed to a font that is identified to correspond to the determined context. The method 1300 continues to block 1306, where a font color is changed to a color that is identified to correspond to the determined context. The method 1300 continues to block 1308, where a font size is changed to a size that is identified to correspond to the determined context. Accordingly, in disclosed embodiments, an electronic device such as a smartphone, can utilize fonts as part of a customization display theme to provide a unique appearance for a user. In one or more embodiments, loading the customization display theme further comprises changing at least one of a font type, a font size, and a font color, at least in part based on the device context.

FIG. 14 depicts a flowchart of a method 1400 by which an electronic device enables customization based on received biometric information including a step rate, according to one or more embodiments. The method 1400 starts at block 1402, where biometric information from the user is received. In one or more embodiments, the biometric information can be obtained from biometric sensor 147 of device 100, and/or a biometric sensor integrated on a communicatively coupled wearable device, such as indicated at 220 of FIG. 2. The biometric data can include, but is not limited to, heart rate, breathing rate, step rate, body temperature, and/or other biometric data. In one or more embodiments, the biometric information obtained by the controller comprises at least one of a heart rate and a step rate. In embodiments, the step rate may be determined by onboard sensors of the device, such as accelerometer 163 and/or gyroscope 164 of device 100. In one or more embodiments, the onboard accelerometer of the device measures acceleration forces in three dimensions (up and down, left and right, forward and backward). When a user takes a step, the accelerometer detects the changes in acceleration and movement. In one or more embodiments, the processor 102 with the device 100 may execute a step detection algorithm to interpret the data from the accelerometer. In one or more embodiments, the algorithm analyzes the patterns in the acceleration data to identify when a step has been taken. The algorithm can include, as inputs, factors such as the frequency, amplitude, and duration of the movements. The method 1400 continues to block 1404 where a step rate is received. In one or more embodiments, based on a number of steps detected in a given time interval (e.g., 60 seconds), a step rate is determined. The method 1400 continues to block 1406 where a check is made to determine if the determined step rate is below a predetermined threshold. In one or more embodiments, the predetermined threshold has a value in the range of 100-120 steps per minute. If, at block 1406, the determined step rate is below the predetermined threshold, then a first background image is rendered at block 1412 as part of loading a first customization display theme. If, at block 1406, the determined step rate is at or above the predetermined threshold, then a second background image is rendered at block 1414 as part of loading a second customization display theme. One or more embodiments can include receiving, via one or more sensors, biometric information of the user; and determining the user context based, in part, on the biometric information. Accordingly, in disclosed embodiments, an electronic device such as a smartphone, can have a customization display theme based on an activity level of the user, where the activity level is based on step rate. As an example, during a period where the step rate is above the predetermined threshold, the displayed image can include people exercising, in order to automatically provide motivational imagery for a user to continue exercising.

FIG. 15 depicts a flowchart of a method 1500 by which an electronic device enables customization based on received biometric information including a heart rate, according to one or more embodiments. The method 1500 starts at block 1502, where biometric information from the user is received. In one or more embodiments, the biometric information can be obtained from biometric sensor 147 of device 100. The biometric data can include, but is not limited to, heart rate, breathing rate, step rate, body temperature, and/or other biometric data. In one or more embodiments, the biometric information obtained by the controller comprises at least one of a heart rate and a step rate. The method 1500 continues with receiving a heart rate at block 1504. In embodiments, the heart rate may be received from a biometric sensor integrated on a communicatively coupled wearable device, such as indicated at 220 of FIG. 2. The biometric sensor on the communicatively coupled wearable device can include a heart rate sensor that utilizes photoplethysmography (PPG) techniques. The heart rate sensor can include one or more light emitting diodes (LEDs) and photodetectors oriented towards the skin of the user. When the LEDs illuminate the skin of the user, a portion of the light is absorbed by the tissues and blood vessels underneath the skin. Based on the changes in light intensity captured by the photodetectors and processed by the PPG algorithm, a heart rate in beats per minute can be determined by analyzing the time intervals between peaks in the PPG signal.

The method 1500 continues to block 1506 where a check is made to determine if the determined heart rate is below a predetermined threshold. In one or more embodiments, the predetermined threshold has a value in the range of 100-120 beats per minute. If, at block 1506, the determined heart rate is below the predetermined threshold, then a first background image is rendered at block 1512 as part of loading a first customization display theme. If, at block 1506, the determined heart rate is at or above the predetermined threshold, then a second background image is rendered at block 1514 as part of loading a second customization display theme. In one or more embodiments, the biometric information is the heart rate, and the method includes receiving the heart rate from a heart rate sensor; comparing the heart rate to a predetermined heartrate threshold; rendering a first background image in response to the heart rate being below a predetermined threshold; and rendering a second background image in response to the heart rate being at or above the predetermined threshold. Accordingly, in disclosed embodiments, an electronic device such as a smartphone, can have a customization display theme based on an activity level of the user, where the activity level is based on heart rate. As an example, during a period where the step rate is above the predetermined threshold, the displayed image can include people exercising, in order to automatically provide motivational imagery for a user to continue exercising.

FIG. 16 depicts a flowchart of a method 1600 by which an electronic device enables customization based on distance from a second electronic device, according to one or more embodiments. The method 1600 starts at block 1602, where a distance from a second electronic device is determined. In one or more embodiments, the distance can be determined via an onboard GPS from each device, such as GPS 160 of device 100 as depicted in FIG. 1. In one or more embodiments, the distance can be computed and/or estimated from a received signal strength indication (RSSI) between the two devices, from Bluetooth® radio signal strength, WiFi radio signal strength, and/or other suitable radio signals. The method 1600 continues to block 1604, where a device context is determined from a user identifier associated with the second electronic device. In one or more embodiments, the user identifier may be derived from a unique identifier of the second electronic device, such as a MAC address, serial number, and/or other uniquely identifying data stored in system memory 120 of communication device 100. In one or more embodiments, the user identifier can be associated with contacts stored within the user device. The contacts have or include associated addresses and/or location markers that can be compared to the current user device location, using GPS or other location determining methods on the user device. The method 1600 continues with obtaining an image associated with the user identifier at block 1606. That is, the device associated with the first user can search for, retrieve, and display an image that includes the second user, who is associated with the second electronic device. In one or more embodiments, obtaining an image associated with the user identifier associated with the second electronic device can include searching through a contact list stored on the device of the user for an image of the user associated with the second electronic device. In one or more embodiments, obtaining an image associated with the user identifier can include searching through a camera roll of images stored on the electronic device. The method 1600 continues with determining if the distance between the (first) electronic device and the second electronic device is less than a predetermined threshold distance. If, at block 1608, the distance is greater than or equal to the predetermined threshold, the method ends. If, at block 1608, the distance is less than the predetermined threshold, the method 1600 continues to block 1610, where the device renders an image on the electronic device as a background image. An example of this is depicted in FIG. 8B, with image 842 of user 804. Accordingly, in disclosed embodiments, an electronic device such as a smartphone, can have a customization display theme based on the proximity of another person, as determined by the proximity of the electronic device associated with the other person.

According to one or more alternate embodiments, the method 1600 can include determining that a distance between the electronic device and an address or location associated with one or more pre-identified contacts is less than a predetermined threshold distance (e.g., 100 m). The method 1600 can then include determining the device context based on an identification of the one or more contacts. The method 1600 can include obtaining an image associated with the one or more contacts and rendering the image as a background image on the display of the electronic device, in response to the distance being less than the predetermined threshold distance. Accordingly, in disclosed embodiments, an electronic device such as a smartphone, can have a customization display theme based on the proximity of another person, as determined by the proximity of the electronic device to an address or location associated with the other person.

Figure 17:
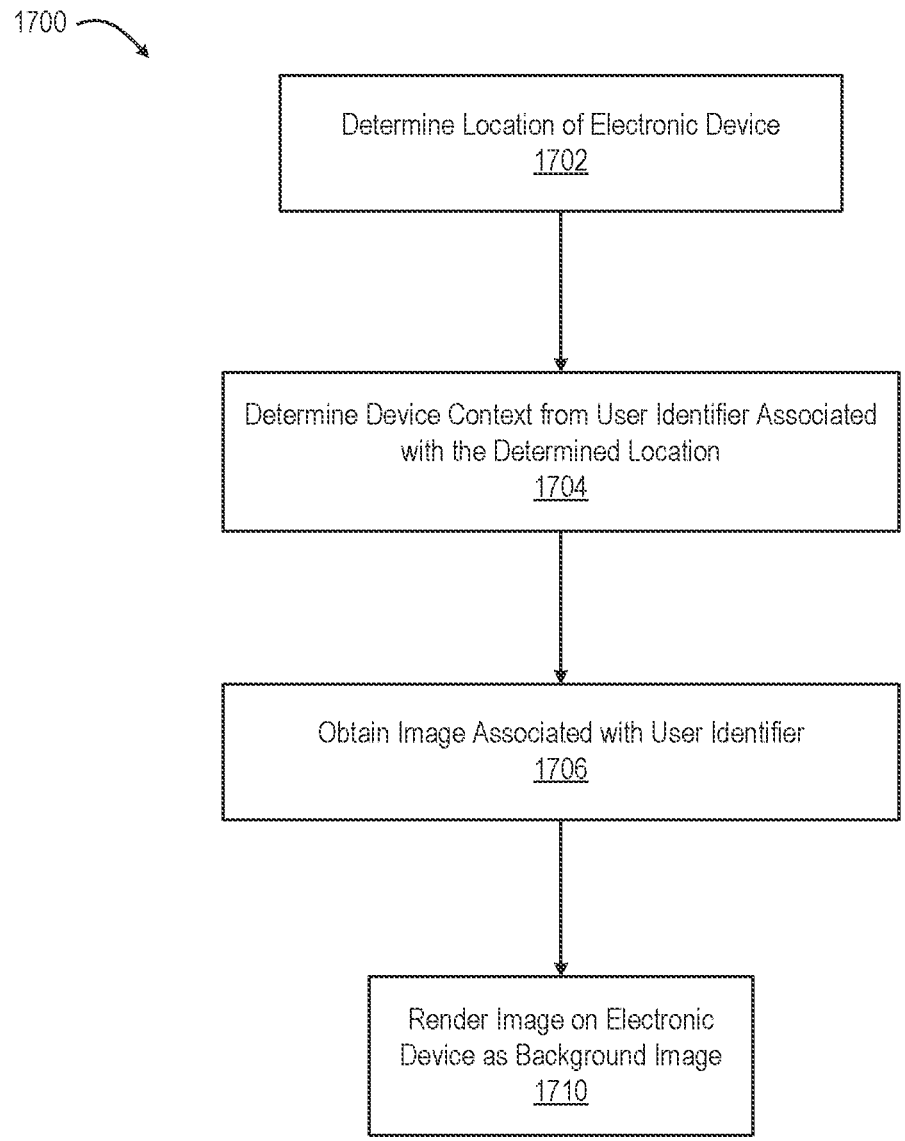
FIG. 17 depicts a flowchart of a method by which an electronic device enables device display screen customization based on a determined location of the electronic device, according to one or more embodiments.

FIG. 17 depicts a flowchart of a method 1700 by which an electronic device enables device display screen customization based on a determined location of the electronic device, according to one or more embodiments. The method 1700 starts at block 1702, where a location of the electronic device is determined. In one or more embodiments, the geographical location can be obtained via a GPS module in the electronic device, similar to as shown at 160 in FIG. 1. The method 1700 continues to block 1704, where a device context is determined, based on a user identifier associated with the determined location. As an example, if a user visits his sister at her home, the location determined by the GPS may correlate with a home address stored in a contact list for the user, corresponding to a contact for his sister. The method 1700 continues to block 1706, where an image associated with the user identifier is obtained. Continuing with the example, an image of the sister can be retrieved from a contacts database, camera roll, or other source. The method 1700 continues to block 1710, where the image obtained at block 1706 is rendered on the display screen of the electronic device as a background image.

As can now be appreciated, disclosed embodiments enable electronic device customization based on a user context and/or a device context. In one or more embodiments, the enabling and/or configuring of the customization display themes of disclosed embodiment is performed via a user interface of the device. Disclosed embodiments enable new levels of automatic customization based on what a user is doing, where the user is, and/or other environmental factors. Thus, disclosed embodiments improve the technical field of customization in electronic devices.

In the above-described methods, one or more of the method processes may be embodied in a computer readable device containing computer readable code such that operations are performed when the computer readable code is executed on a computing device. In some implementations, certain operations of the methods may be combined, performed simultaneously, in a different order, or omitted, without deviating from the scope of the disclosure. Further, additional operations may be performed, including operations described in other methods. Thus, while the method operations are described and illustrated in a particular sequence, use of a specific sequence or operations is not meant to imply any limitations on the disclosure. Changes may be made with regards to the sequence of operations without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object-oriented programming language, without limitation. These computer program instructions may be provided to a processor of a general-purpose computer, special-purpose computer, or other programmable data processing apparatus to produce a machine that performs the method for implementing the functions/acts specified in the flowchart and/or block diagram block or blocks. The methods are implemented when the instructions are executed via the processor of the computer or other programmable data processing apparatus.

As will be further appreciated, the processes in embodiments of the present disclosure may be implemented using any combination of software, firmware, or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device can include the following: a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage device may be any tangible medium that can contain or store a program for use by or in connection with an instruction execution system, apparatus, or device.

Where utilized herein, the terms "tangible" and "non-transitory" are intended to describe a computer-readable storage medium (or "memory") excluding propagating electromagnetic signals, but are not intended to otherwise limit the type of physical computer-readable storage device that is encompassed by the phrase "computer-readable medium" or memory. For instance, the terms "non-transitory computer readable medium" or "tangible memory" are intended to encompass types of storage devices that do not necessarily store information permanently, including, for example, RAM. Program instructions and data stored on a tangible computer-accessible storage medium in non-transitory form may afterwards be transmitted by transmission media or signals such as electrical, electromagnetic, or digital signals, which may be conveyed via a communication medium such as a network and/or a wireless link.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

As used herein, the term "or" is inclusive unless otherwise explicitly noted. Thus, the phrase "at least one of A, B, or C" is satisfied by any element from the set {A, B, C} or any combination thereof, including multiples of any element.

While the disclosure has been described with reference to example embodiments, it will be understood by those skilled in the art that various changes may be made and equivalents may be substituted for elements thereof without departing from the scope of the disclosure. In addition, many modifications may be made to adapt a particular system, device, or component thereof to the teachings of the disclosure without departing from the scope thereof. Therefore, it is intended that the disclosure not be limited to the particular embodiments disclosed for carrying out this disclosure, but that the disclosure will include all embodiments falling within the scope of the appended claims.

What is claimed is:

1. An electronic device comprising:
    an electronic display;
    at least one image capturing device that captures and produces image content;
    a controller communicatively coupled to the at least one image capturing device and the electronic display, and which:
        in response to detecting a self-photo of a user in received image content from the at least one image capturing device:
        determines a user context from information within the received image content; and
        loads a customization display theme for the electronic device, based on the user context, wherein the customization display theme includes one or more theme elements.

2. The electronic device of claim 1, wherein to determine the user context, the controller identifies apparel worn by the user, and renders an image corresponding to the identified apparel on the electronic display.

3. The electronic device of claim 2, wherein the controller:
    identifies a color within the apparel worn by the user; and
    renders a background image that includes a similar color to the color of the identified apparel.

4. The electronic device of claim 1, wherein the controller:
    receives, via one or more sensors, biometric information of the user; and
    determines the user context based, in part, on the biometric information.

5. The electronic device of claim 4, wherein the biometric information obtained by the controller comprises at least one of a heart rate and a step rate.

6. The electronic device of claim 5, wherein:
    the biometric information is the heart rate; and
    to load a customization display theme for the electronic device, the controller:
        receives the heart rate from a heart rate sensor;
        compares the heart rate to a predetermined heartrate threshold;
        renders a first background image in response to the heart rate being below a predetermined threshold; and
        renders a second background image in response to the heart rate being at or above the predetermined threshold.

7. The electronic device of claim 1, further comprising an audio capturing device communicatively coupled to the controller, and wherein determining the user context is further based on received audio content from the audio capturing device.

8. The electronic device of claim 1, further comprising:
    a communication interface that enables the electronic device to connect to, and transmit instructions to a second electronic device; and
    wherein the controller transmits instructions to the second electronic device to cause the second electronic device to load a second customization display theme on the second electronic device, wherein the second customization display theme includes one or more theme elements that correspond to the customization display theme of the electronic device.

9. A method comprising:
    detecting, by at least one processor of an electronic device that comprises an electronic display and an image capturing device, a self-photo within received image content from the image capturing device;
    determining a user context for a user from information within the received image content; and
    loading a customization display theme for the electronic device, based on the user context,
    wherein the customization display theme includes one or more theme elements.

10. The method of claim 9, further comprising:
    identifying apparel worn by the user; and
    rendering an image corresponding to the identified apparel on the electronic display.

11. The method of claim 10, further comprising:
    identifying a color within the apparel worn by the user; and
    wherein rendering the image comprises rendering a background image that includes a similar color to the color of the identified apparel.

12. The method of claim 9, further comprising:
    receiving, via one or more sensors, biometric information of the user; and
    determining the user context based, in part, on the biometric information.

13. The method of claim 12, wherein the biometric information obtained comprises at least one of a heart rate and a step rate.

14. The method of claim 13, wherein the biometric information is the heart rate, comprising:
    receiving the heart rate from a heart rate sensor;
    comparing the heart rate to a predetermined heartrate threshold;
    rendering a first background image in response to the heart rate being below a predetermined threshold; and rendering a second background image in response to the heart rate being at or above the predetermined threshold.

15. The method of claim 9, wherein determining the user context is further based on received audio content from an audio capturing device communicatively coupled to the at least one processor.

16. The method of claim 9, further comprising transmitting instructions to a second electronic device to cause the second electronic device to load a second customization display theme on the second electronic device, wherein the second customization display theme includes one or more theme elements that correspond to the customization display theme of the electronic device.

17. A computer program product comprising a non-transitory computer readable medium having program instructions that when executed by a processor of an electronic device that comprises an electronic display and an image capturing device that produces image content, configures the electronic device to perform functions comprising:
    detecting a self-photo within received image content from the image capturing device;
    determining a user context for a user from information within the received image content; and
    loading a customization display theme for the electronic device, based on the user context, wherein the customization display theme includes one or more theme elements.

18. The computer program product of claim 17, wherein the computer program product further comprises program instructions for:
    identifying apparel worn by the user; and
    rendering an image corresponding to the identified apparel on the electronic display.

19. The computer program product of claim 18, wherein the computer program product further comprises program instructions for:
    identifying a color within the apparel worn by the user; and
    rendering a background image that includes a similar color to the color of the identified apparel.

20. The computer program product of claim 17, wherein the computer program product further comprises program instructions for:
    receiving, via one or more sensors, biometric information of the user; and
    determining the user context based, in part, on the biometric information.

* * * * *